(12) United States Patent
Hollenberg et al.

(10) Patent No.: US 8,766,630 B2
(45) Date of Patent: Jul. 1, 2014

(54) METHOD AND APPARATUS FOR MONITORING A PROPERTY OF A SAMPLE

(75) Inventors: Lloyd Hollenberg, Carlton (AU); Jared Cole, Carlton (AU)

(73) Assignee: The University of Melbourne, Parkville (AU)

(*) Notice: Subject to any disclaimer, the term of this patent is extended or adjusted under 35 U.S.C. 154(b) by 545 days.

(21) Appl. No.: 13/127,317

(22) PCT Filed: Nov. 4, 2009

(86) PCT No.: PCT/AU2009/001434
§ 371 (c)(1),
(2), (4) Date: Sep. 8, 2011

(87) PCT Pub. No.: WO2010/051580
PCT Pub. Date: May 14, 2010

(65) Prior Publication Data
US 2012/0019242 A1    Jan. 26, 2012

(30) Foreign Application Priority Data

Nov. 4, 2008   (AU) ............................... 2008905684

(51) Int. Cl.
*G01R 33/20* (2006.01)
*G01R 33/32* (2006.01)
*G01Q 70/14* (2010.01)
*G01N 24/10* (2006.01)
*G01Q 60/00* (2010.01)
*B82Y 15/00* (2011.01)
*B82Y 35/00* (2011.01)

(52) U.S. Cl.
CPC .............. *G01Q 70/14* (2013.01); *B82Y 15/00* (2013.01); *G01R 33/326* (2013.01); *B82Y 35/00* (2013.01); *G01N 24/10* (2013.01); *G01Q 60/00* (2013.01)

USPC .......................................... 324/300; 324/318

(58) Field of Classification Search
USPC ......................... 324/300–322; 600/407–455
See application file for complete search history.

(56) References Cited

U.S. PATENT DOCUMENTS 3,892,485 A  *  7/1975  Merritt et al. ................. 356/339
4,142,416 A  *  3/1979  Smith et al. ...................... 436/7

(Continued)

FOREIGN PATENT DOCUMENTS

WO       2009/073736 A1    6/2009

OTHER PUBLICATIONS

Jared H. Cole and Lloyd L. Hollenberg, "Scanning Quantum Decoherence Microscopy," (online), arXiv:0811.1913v1 [quant-ph], Nov. 12, 2008. Retrieved from the Internet Dec. 11, 2009 <URL:http://lanl.arxiv.org/PS_cache/arxiv/pdf/0811/0811.1913v1.pdf> Abstract, pp. 1-8.

(Continued)

*Primary Examiner* — Melissa Koval
*Assistant Examiner* — Rishi Patel
(74) *Attorney, Agent, or Firm* — Kelly & Kelley, LLP

(57) ABSTRACT

The present disclosure provides a method of monitoring a property of a sample, such as a nanoscopic property of the sample. The method comprises the steps of providing a quantum probe having a quantum state and exposing the quantum probe to the sample in a manner such that the property of the sample, in the proximity of the quantum probe, affects quantum coherence of the quantum probe. The method also comprises detecting a rate of quantum decoherence of the quantum probe to monitor the property of the sample. Further the present disclosure provides an apparatus for monitoring a property of a sample.

27 Claims, 18 Drawing Sheets

(56) References Cited

U.S. PATENT DOCUMENTS

| | | | |
|---|---|---|---|
| 6,218,832 B1* | 4/2001 | Chuang et al. | 324/300 |
| 6,528,997 B2 | 3/2003 | Zhong et al. | |
| 7,328,059 B2* | 2/2008 | Sevick-Muraca et al. | 600/473 |
| 7,521,928 B2* | 4/2009 | Romalis et al. | 324/304 |
| 8,467,842 B2* | 6/2013 | Hegg et al. | 600/310 |
| 2007/0194225 A1* | 8/2007 | Zorn | 250/306 |
| 2007/0215861 A1 | 9/2007 | Stafford et al. | |

OTHER PUBLICATIONS

Laim T. Hall, Jared H. Cole, Charles D. Hill and Lloyl C.L. Hollenberg, "Sensing of Fluctuating Nanoscale Magnetic Fields Using NV Centres in Diamond," (online), arXiv:0907.2292v1 [cond-mat.mes-hall], Jul. 14, 2009. Retrieved from the Internet Dec. 11, 2009 <URL:http://lanl.arxiv.org/PS_cache/arxiv/pdf/0907/09072292v1.pdf> Abstract, pp. 1-4.

* cited by examiner (b)

Confocal scan of fluorescing NV
nanocrystals (micron scale), typically 50nm
in size.

(a)

(a)

(b)

(c)

(a)

(b)

METHOD AND APPARATUS FOR MONITORING A PROPERTY OF A SAMPLE

TECHNICAL FIELD

The present invention relates to a method and apparatus for monitoring a property of a sample. The present invention relates particularly, though not exclusively, to a method and apparatus for monitoring a nanoscopic property of a sample.

BACKGROUND ART

Advancement of our understanding of biological and condensed matter systems would greatly benefit from an ability to monitor the structure and dynamics at a molecular level. For example, cell membranes include ion channels and detailed information concerning the activity of the ion channels would be very useful for advancing our understanding of the function of cell membranes and cells.

Two stage quantum probes have been used as a sensitive spatial electrometer or magnetometer to produce images. However, the methods known to date do not allow monitoring processes and dynamics at the nanoscale in a satisfactory manner. There is a need for technological advancement.

SUMMARY OF THE INVENTION

The present invention provides in a first aspect a method of monitoring a property of a sample, the method comprising the steps of:

providing a quantum probe having a quantum state;
exposing the quantum probe to the sample in a manner such that the property of the sample, in the proximity of the quantum probe, affects quantum coherence of the quantum probe; and
detecting a rate of quantum decoherence of the quantum probe to monitor the property of the sample.

The property of the sample typically is a nanoscopic property.

The present invention opens new avenues in science and technology. The property may relate to a local atomic of molecular property of the sample, such as an electric or a magnetic property. The nanoscopic property may relate to a fundamental spin, such as the spin of an ion, or a charge or a collection thereof. For example, the ion may move thorough an ion channel of a cell membrane in the proximity surface of the quantum probe. The ion influences the decoherence rate of the quantum probe and consequently is detectable using the method in accordance with the embodiments of the present invention and can be resolved both spatially and temporally. In another example the spin may be the spin of a free-radical particle moving in a biological structure.

Quantum probes, for example quantum qubits in quantum information applications, are generally isolated as far as possible from the environment in order to maintain quantum coherence. Embodiments of the present invention are consequently counterintuitive as they deliberately cause decoherence of the quantum probe and use detection of the decoherence rate to detect properties of the samples in a unique manner.

The quantum probe may comprise a two-state quantum probe (qubit) or multi-state quantum probe, for instance a charge state qubit, or may comprise a number of quantum systems that may be entangled. The quantum probe may be based on electric charge or magnetic spin degrees of freedom. Alternatively, the quantum probe may be any other suitable type of quantum probe.

The quantum probe may be movable relative to the sample or may be stationary relative to the sample. The quantum probe may also be incorporated in the sample.

The quantum probe may comprise a quantum system consisting of a single particle, such as an atom or ion, or comprising a plurality of particles, a portion of a material, a crystal and/or may be positioned in a matrix of a surrounding material. Further, the quantum probe may comprise a plurality of particles sharing a quantum entangled state.

The quantum probe may also be one of a plurality of quantum probes and the step of providing the quantum probe may comprise providing a plurality of quantum probes, such as an array of the quantum probes. The plurality of quantum probes may comprise any number of quantum probes.

The step of detecting a rate of quantum decoherence may comprise detecting photons emitted from the plurality of quantum probes. For example, if the quantum probes are provided in the form of an array, the step of setecting the photons may comprise use of a corresponding array of respective detectors.

The quantum probe may comprise one quantum system or a plurality of quantum systems and the step of exposing the quantum probe to the sample may comprise exposing the probe to property of a sample, such as a nanoscopic property associated with single particles or a small group of particles. For example, the nanoscopic property of the sample may be associated with the spin of an ion or a small groups of ions. Alternatively, the quantum probe may also comprise one quantum system or a plurality of quantum systems, but the step of exposing the quantum probe to the sample may comprise exposing the probe to a larger scale property, such as a microscopic or macroscopic property which may be associated with a larger group of particles or with a bulk property of the sample.

In one specific example the quantum probe comprises a diamond material having at least one nitrogen-vacancy (NV) centre. The quantum probe may comprise one NV centre, but may alternatively also comprise a plurality of NV centres in the diamond material.

The step of providing the quantum probe may comprise transforming the quantum probe into a predefined quantum state, for example a superposition or entangled state in which the quantum probe may be particularly sensitive to magnetic fields. Transforming the quantum probe may comprise the application of suitable radiation. For example, if the quantum probe comprises a NV centre, the step of transforming the quantum probe may comprise exposing the NV-centre to suitable microwave radiation to generate a suitable quantum state of Zeeman energy levels. Further, the method may comprise optically pumping the NV-centre, which may comprise use of a suitable laser such as a laser having a wavelength of the order of 520 nm. The step of detection a decoherence rate may comprise detecting fluorescence photons emitted from the NV-centre.

Then method may also comprise the step of controlling the quantum state of the quantum probe by applying suitable radiation. For example, the method may comprise the step of controlling quantum coherence time of the quantum probe by applying suitable radiation.

The method typically comprises the step of moving the quantum probe and the sample relative to each other and performing the method so that the decoherence rate is detectable at a plurality of sample locations. In this case the method typically comprises the step of generating a line scan or a map of a portion of the sample and showing a distribution of decoherence properties. For example, the method may comprise scanning the quantum probe with NV centre across the surface of the sample.

In one specific embodiment of the present invention the method allows monitoring a function of biological samples typically at the nanoscale. The method may comprise detecting fluctuations or particle, such as ions, in the surface or bulk of the sample. The sample may for example be a cell membrane and may comprise a bi-lipid. The sample may comprise ion channels, such as channels though which single ions diffuse. The method may comprise exposing the sample, or the sample and the quantum probe, to a liquid, such as water, a salt-containing solution, or any other suitable solution. The method may further comprise detecting a change (usually an increase) in quantum decoherence rate caused by an influence of a spin of the particle on the quantum probe and thereby monitoring for example the function of the ion channel. The spin may be a nuclear spin of the particle.

In other embodiments the method may also comprise combining generated decoherence rate maps with maps of other properties, such maps showing electric, magnetic or structural sample properties, which is particularly advantageous for characterising solid state samples. The method may further comprise generating a map of an effective quantum Hamiltonian as a function of position on the sample. Combining a map of the decoherence rate with a map of the Hamiltonian may provide an image of the sample surface that is a direct window into the distribution and sources of magnetic or electric field fluctuations emanating from the sample surface.

The present invention provides in a second aspect and apparatus for monitoring a property of a sample, the apparatus comprising:
  a quantum probe that has quantum state;
  a holder for holding the quantum probe in the proximity of a sample so that the quantum coherence of the quantum probe is influenced by the property of the sample; and
  a detector for detecting a quantity indicative of a quantum decoherence rate and thereby monitoring the property of the sample.

The property of the sample typically is a nanoscopic property.

The apparatus typically also comprises a source for transforming the quantum probe into the quantum state.

The holder of the apparatus typically comprises a scanning arrangement that is suitable for scanning the quantum probe and the sample relative to each other. In one specific example the holder comprises an arrangement similar to an atomic force microscope.

In one specific embodiment of the present invention the quantum probe comprises a diamond material having one or a plurality of NV centres. In this case the source for transforming the quantum probe typically comprises a source for emitting microwave radiation suitable for generating a Zeeman shift of energy levels and/or controlling the quantum state of the quantum probe, for example controlling a coherence time of the quantum probe. Further, the apparatus typically comprises an optical light source for optically pumping the at least one NV-centre. The detector typically is a photon detector arranged to detect fluorescence photons emitted from the at least one NV-centre.

The quantum probe may be movable relative to the sample or may be stationary relative to the sample. The quantum probe may also be incorporated in the sample.

The quantum probe may comprise one quantum system or a plurality of quantum systems.

The quantum probe may comprise a quantum system consisting of a single particle such as an atom or ion, or comprising a plurality of particles, a portion of a material, a crystal and/or may be positioned in a matrix of a surrounding material. Further, the quantum probe may comprise a plurality of particles sharing a quantum entangled state.

The quantum probe may also be one of a plurality of quantum probes and the step of providing the quantum probe may comprise providing a plurality of quantum probes, such as an array of the quantum probes. The plurality of quantum probes may comprise any number of quantum probes.

The detector may also comprise a plurality of detector elements. For example, if the quantum probes are provided in the form of an array, the detector may comprise an array of respective detector elements.

The invention will be more fully understood from the following description of specific embodiments of the invention. The description is provided with reference to the accompanying drawings.

BRIEF DESCRIPTION OF THE DRAWINGS

FIG. 7($b$) is a schematic diagram showing a cell membrane nearby the diamond nanocrystal of FIG. 7($a$) which is host to channels permitting the flow of ions across the surface (The ion motion results in an effective fluctuating magnetic field at the NV position which decoheres the quantum state of the NV system);

FIG. 7($c$) is a three-dimensional representation of decoherence results in a decrease in fluorescence, which is most pronounced in regions close to the ion channel opening;

FIG. 7($d$) is a two dimensional plot of ion channel state against time showing that changes in fluorescence also permit the temporal tracking of ion channel dynamics;

FIG. 8($b$) is an energy level schematic diagram of the $C_{3v}$-symmetric NV system showing NV spin detection through optical excitation and emission cycle (Magnetic sublevels $m_s=0$ and $m_s=\pm1$ are split by D=2.88 GHz in the crystal field. Degeneracy between the $m_s=\pm1$ sublevels is lifted by a Zeeman shift, $\delta\omega$. Application of 532 nm green light induces a spin-dependent photoluminescence and pumping into the $m_s=0$ ground state);

FIG. 8($c$) is a two-dimensional graph showing a specific microwave and optical pulse sequence for coherent control and readout;

FIG. 12(a) is a two dimensional plot showing the dependence of temporal resolution ($\delta t$) and signal variance ($\delta P$) on the number of data points included in the running average ($N_s$);

FIG. 12(b) is a two dimensional plot showing simulated reconstruction of a sodium ion channel signal with a 200 Hz switching rate using optical readout of an NV centre (blue curve) (The actual ion channel state (on/off) is depicted by the dashed line, and the green line depicts the analytic confidence threshold);

FIG. 13 (b) shows diamond crystals having NV-centres in accordance with a specific embodiment of the present invention;

DETAILED DESCRIPTION OF SPECIFIC EMBODIMENTS

Referring initially to FIG. 1 to 4, operation and function of an apparatus for monitoring a property of a sample in accordance with a specific embodiment of the present invention are initially briefly summarised. The apparatus comprises a diamond crystal containing a nitrogen-vacancy (NV) spin qubit on a nano-scanning tip, microwave spin control, and confocal optical spin readout.

Figure 2:
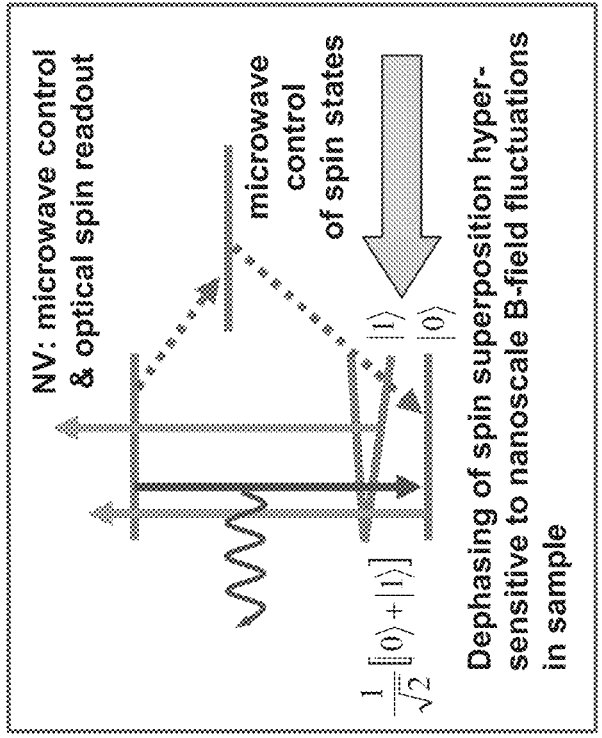
FIG. 2 illustrates energy states of a quantum probe accordance with an embodiment of the present invention.
Figure 1:
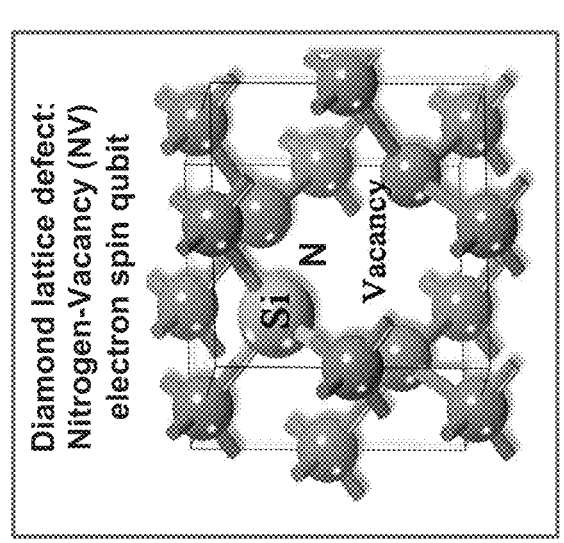
FIG. 1 illustrates an NV-centre of a quantum probe in accordance with an embodiment of the present invention.

FIG. 1 illustrates the NV lattice defect, which has a relatively long coherence times (ms range) at room temperature. FIG. 2 shows energy levels of the NV-centre as affected by suitable microwave radiation. Ground state Zeeman levels are put into a superposition state by the microwave radiation. After interaction with the sample the state is read-out systematically to determine the local decoherence rate, which is highly sensitive to effective magnetic field fluctuations at the nanoscale. The read-out involves use of a laser (not shown) having a wavelength of approximately 520 nm.

Figure 3:
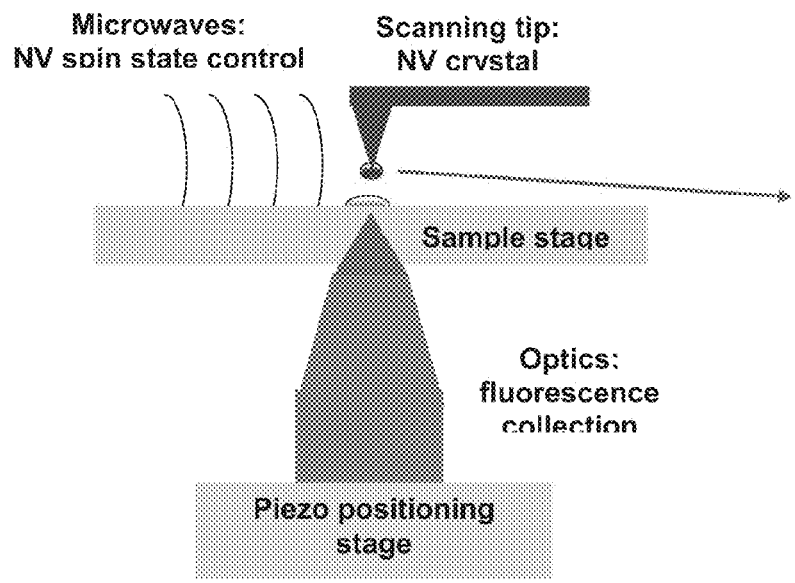
FIG. 3 shows an apparatus for monitoring a property of a sample accordance with an embodiment of the present invention.

FIG. 3 illustrates the NV system being scanned over a sample. In this example the sample includes a membrane ion-channel. Nuclear spins of the (electron-spin paired) ions form a fluctuating spin current, which dephases the NV spin states over a characteristic timescale.

Figure 4:
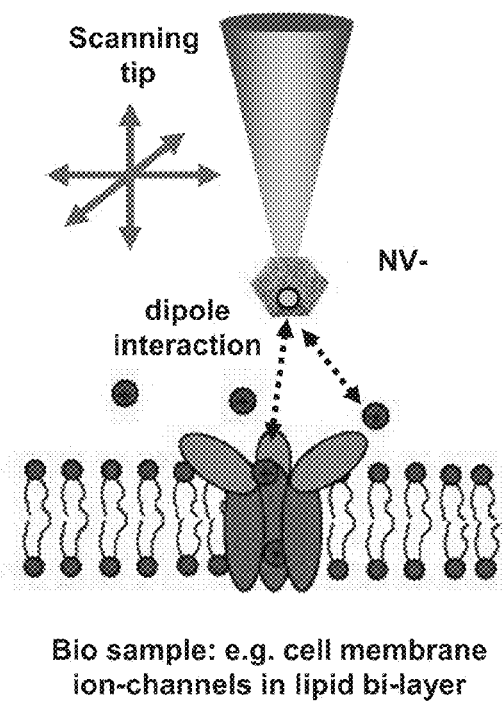
FIG. 4 illustrates interaction of a biological sample with the quantum probe accordance with an embodiment of the present invention.
Figure 5:
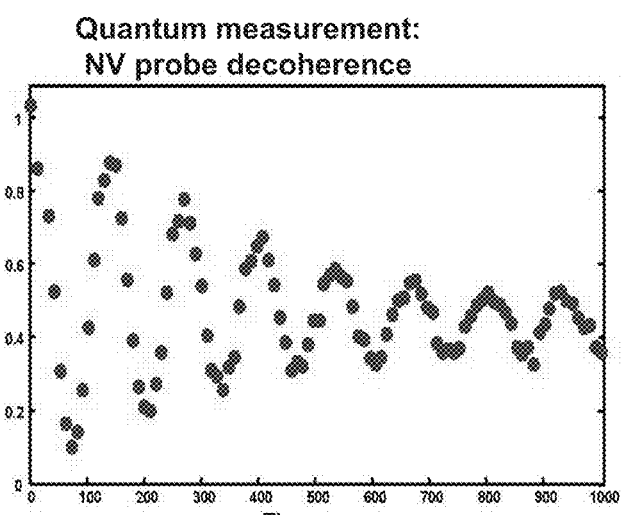
FIG. 5 shows a measurement illustrating loss of decoherence with time (arbitrary units)

FIG. 4 illustrates the interaction of the quantum probe with the ion-channel and FIG. 5 shows a measurement illustrating loss of quantum coherence with time (arbitrary units).

Figure 6:
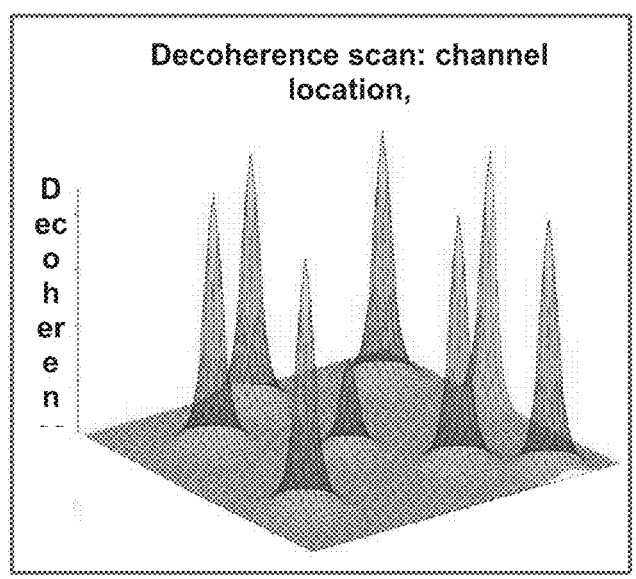
FIG. 6 shows a simulated map having 7 decoherence rate maxima associated with locations of ion channels (arbitrary units)

FIG. 6 shows a simulated map having 7 maxima that coincide with locations of ion cannels. The simulations for generation of the map take into account various background sources of dephasing (diffusion of electrolytic and lipid bilayer components) and their associated (fast) timescales show that the operation of a single ion channel (or several) can be detected and resolved spatially and temporally in a scanning decoherence measurement forming a unique image of bio-function at the nanoscale.

Referring now to FIG. 7 to 12, apparatus and methods for monitoring a property of a sample in accordance with another specific embodiment of the present invention are described.

In drug discovery research there is a need for non-invasive detection of cell membrane ion channel operation with wide-field capability [65]. Existing techniques are generally invasive [66], require specialized nano structures [67-70], or are only applicable to certain ion channel species [71]. Quantum nanotechnology may be used to address at least some of these problems. The nitrogen-vacancy (NV) centre in nano-diamond is currently of great interest as a novel single atom quantum probe for nanoscale processes [72-84]. However, until now, beyond the use of diamond nanocrystals as fluorescence markers [73-77], nothing was known about the quantum behaviour of a NV probe in the complex room temperature extra-cellular environment. What follows is an exploration of the quantum dynamics of a NV probe in proximity to the ion channel, lipid bilayer and surrounding aqueous environment. Results indicate that real-time detection of ion channel operation at millisecond resolution is possible by directly monitoring the quantum decoherence of the NV probe. With the potential to scan and scale-up to an array-based system this conclusion may have wide ranging implications for nanoscale biology and drug discovery.

The cell membrane is a critical regulator of life. Its importance is reflected by the fact that the majority of drugs target membrane interactions [69]. Ion channels allow for passive and selective diffusion of ions across the cell membrane [86], while ion pumps actively create and maintain the potential gradients across the membranes of living cells [87]. To monitor the effect of new drugs and drug delivery mechanisms a wide field ion channel monitoring capability is essential. However, there are significant challenges facing existing techniques stemming from the fact that membrane proteins, hosted in a lipid bilayer, require a complex environment to preserve their structural and functional integrity. Patch clamp techniques are generally invasive, quantitatively inaccurate, and difficult to scale up [87-89], while black lipid membranes [90,91] often suffer from stability issues and can only host a limited number of membrane proteins.

Instead of altering the way ion channels and the lipid membrane are presented or even assembled for detection, the approach described herein is to consider a novel and inherently non-invasive in-situ detection method based on the quantum decoherence of a single-atom probe [78]. In this context, decoherence refers to the loss of quantum coherence between magnetic sub-levels of a controlled atom system due to interactions with an environment. Such superpositions of quantum states are generally fleeting in nature due to interactions with the environment, and the degree and timescale over which such quantum coherence is lost can be measured precisely. The immediate consequence of the fragility of the quantum coherence phenomenon is that detecting the loss of quantum coherence (decoherence) in a single atom probe offers a unique monitor of biological function at the nanoscale.

Figure 7:
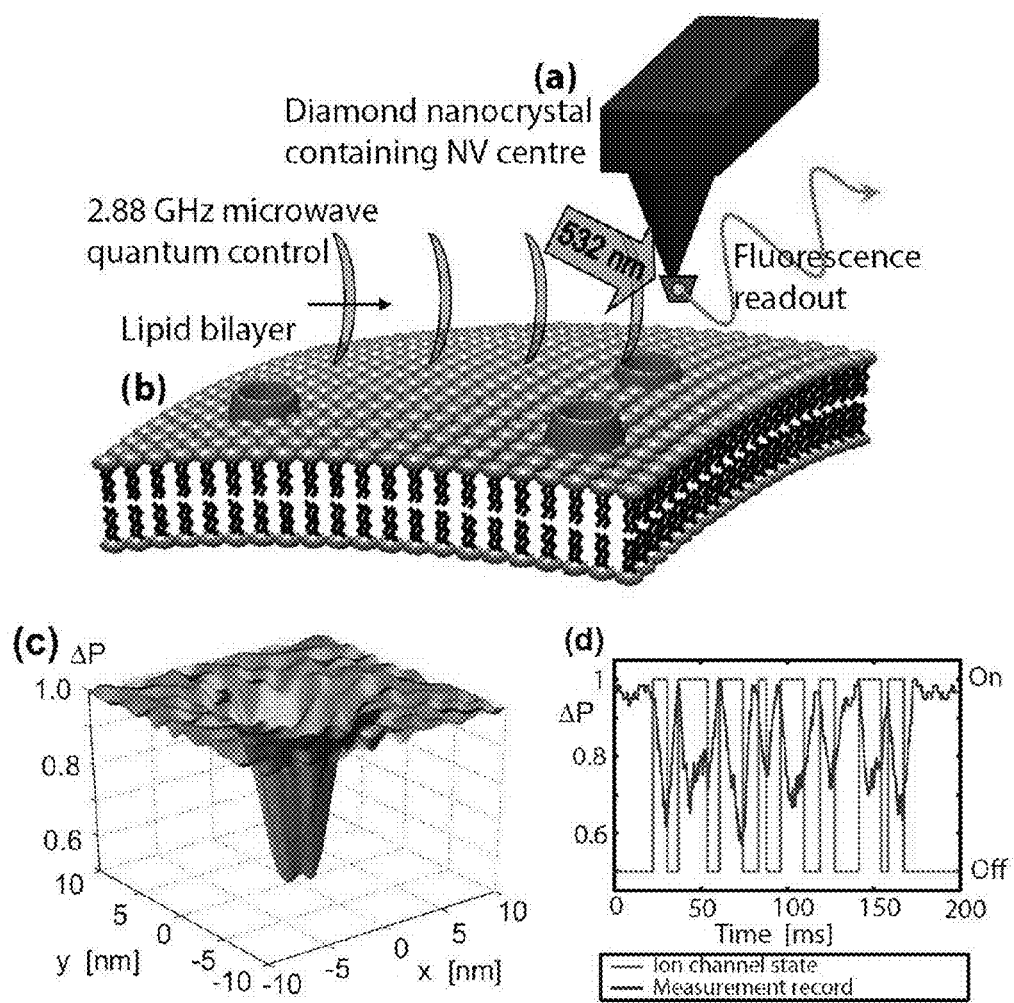
FIG. 7($a$) is a schemtaic diagram showing a single nitrogen-vacancy (NV) defect in a diamond nanocrystal placed on an AFM tip (The unique properties of the NV atomic level scheme allows for optically induced readout and microwave control of magnetic (spin) sub-levels)
Figure 8:
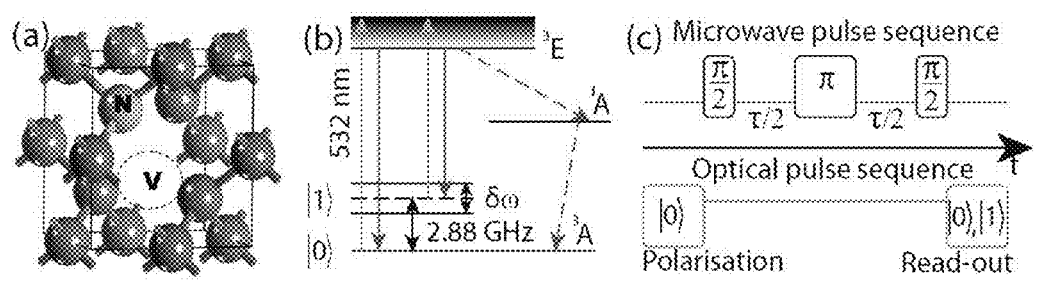
FIG. 8($a$) is a schemtaic diagram showing a NV-centre diamond lattice defect.

The NV probe [FIG. 7] consists of a nano-crystal of diamond containing a nitrogen-vacancy (NV) defect placed at the end of an AFM tip, as recently demonstrated [72]. For biological applications a quantum probe must be submersible to be brought within nanometers of the sample structure, hence the NV system locked and protected in the ultra-stable diamond matrix [FIG. 7(a)] is the system of choice. Of all the atomic systems known, the NV centre in diamond alone offers the controllable, robust and persistent quantum properties such room temperature nano-sensing applications will demand [73,74,92], as well as zero toxicity in a biological environment [77,92,93]. Theoretical proposals for the use of diamond nanocrystals containing a NV system as sensitive nanoscale magnetometers [79-81] have been followed closely by demonstrations in recent proof-of-principle experiments [72,82,83]. However, such nanoscale magnetometers employ only a fraction of the potential of the quantum resource at hand and do not have the sensitivity to detect the minute magnetic moment fluctuations associated with ion channel operation. In contrast, results described below show that measuring the quantum decoherence of the NV induced by the ion flux provides a highly sensitive monitoring capability for the ion channel problem, well beyond the limits of magnetometer time-averaged field sensitivity [84].

In order to determine the sensitivity of the NV probe to the ion channel signal the lipid membrane, embedded ion channels, and the immediate surroundings are described as a fluctuating electromagnetic environment and quantitatively assess each effect on the quantum coherence of the NV centre. The net magnetic field due to diffusion of nuclei, atoms and molecules in the immediate surroundings of the nanocrystal containing the NV system and the extent to which each source will decohere is considered to be the quantum state of the NV. Over and above these background sources, the decoherence of the NV spin levels is in fact highly sensitive to the particular signal due to the ion flux through a single ion channel. Theoretical findings demonstrate the potential of this approach to revolutionize the way ion channels and potentially other membrane bound proteins or interacting species are characterized and measured, particularly when scale-up and scanning capabilities are considered.

In the following, the quantum decoherence imaging system is described with reference to FIG. 7 and being implemented using an NV centre in a realistic technology platform. The biological system is described, considering the various sources of magnetic field fluctuations due to atomic and molecular processes in the membrane itself and in the surrounding media; and their effect on the decoherence of the optically monitored NV system. Estimates of the sensitivity of the NV decoherence to various magnetic field fluctuation regimes (amplitude and frequency) are made which indicate the ability to detect ion channel switch-on/off events. Also described are large scale numerical simulations of the time evolution of the NV spin system including all magnetic field generating processes. This acts to verify the analytic picture, and provides quantitative results for the monitoring and scanning capabilities of the system.

The energy level scheme of the $C_{3v}$-symmetric NV system [FIG. 8(b)] consists of ground ($^3A$), excited ($^3E$) and metastable ($^1A$) states. The ground state manifold has spin sub-levels (m=0,±), which in zero field are split by 2.88 GHz. In a background magnetic field the lowest two states (m=0.1) are readily accessible by microwave control. An important property of the NV system is that under optical excitation the spin levels are readily distinguishable by a difference in fluorescence, hence spin-state readout is achieved by purely optical means [94,95]. Because of this relative simplicity of control and readout, the quantum properties of the NV system, including the interaction with the immediate crystalline environment, have been well probed [96,97]. Remarkably for the decoherence imaging application, the coherence time of the spin levels is very long even at room temperature: in type 1b nanocrystals $T_2 \sim 1$ μs, and in isotopically engineered diamond can be as long as 1.8 ms [83] with the use of a spin-echo microwave control sequence [FIG. 8(c)].

Typical ion channel species $K^+$, $Ca^{2+}$, $Na^+$, and nearby water molecules are electron spin paired, so any magnetic signal due to ion channel operation will be primarily from the motion of nuclear spins. Ions and water molecules enter the channel in thermal equilibrium with random spin orientations, and move through the channel over a μs timescale. The monitoring of ion channel activity occurs via measurement of the contrast in probe behavior between the on and off states of the ion channel. This then requires the dephasing due to ion channel activity to be at least comparable to that due to the fluctuating background magnetic signal. The decoherence of the NV quantum state due to the diffusion of water molecules, buffer molecules, saline components as well as the transversal diffusion of lipid molecules in the cell membrane must therefore be accounted for.

The nth nuclear spin with charge $q_n$, gyromagnetic ratio $\gamma_n$, velocity $\vec{v}_n$ and spin vector $\vec{S}_n$, interacts with the NV spin vector $\vec{P}$ and gyromagnetic ratio $\gamma_p$ through the time-dependent dipole dominated interaction:

$$H_{int}(t) = \sum_{n=1}^{n} \kappa_{dip}^{(n)} [\vec{P} \cdot \vec{S}_n r_n^3(t) - 3\vec{P} \cdot \vec{r}_n(t)\vec{S}_n \cdot \vec{r}_n(t)r_n^3(t)] \quad (1)$$

where $\kappa_{dip}^{(n)} \equiv \mu_0 4\pi\hbar^2 \gamma_p \gamma_n$ are the probe-ion coupling strengths, and $\vec{r}_n(t)$ is the time-dependent ion-probe separation. Additional Biot-Savart fields generated by the ion motion, both in the channel and the extracellular environment, are several orders of magnitude smaller than this dipole interaction and are neglected here. Any macroscopic fields due to intracellular ion currents are of nano-Tesla (nT) order and are effectively static over $T_2$ timescales. These effects will thus be suppressed by the spin-echo pulse sequence.

FIG. 9(a) shows typical field traces at a probe height of 1-10 nm above the ion channel, generated by the ambient environment and the on-set of ion-flow as the channel opens. The contribution to the net field at the NV probe position from the various background diffusion processes dominate the ion channel signal in terms of their amplitude. Critically, since the magnetometer mode detects the field by acquiring phase over the coherence time of the NV centre, both the ion channel signal and background are well below the nT $Hz^{-1/2}$ sensitivity limit of the magnetometer over the (~1 ns) self-correlated timescales of the environment. However, the effect of the various sources on the decoherence rate of the NV centre are distinguishable because the amplitude-fluctuation frequency scales are very different, leading to remarkably different dephasing behaviour.

To understand this effect, it is useful to consider the full quantum evolution of the NV probe. In the midst of this environment the probe's quantum state, described by the density matrix ρ(t), evolves according to the Liouville equation, $(d/dt)\rho(t) = -i\hbar[H(t)\rho(t) - \rho(t)H(t)]$, where ρ(t) is the incoherent thermal average over all possible unitary evolutions of the entire system, as described by the full Hamiltonian, $H = H_{nv} + H_{int} + H_{bg}$, where $H_{nv}$ is the Hamiltonian of the NV system, and $H_{int}$ describes the interaction of the NV system with the background environment (e.g. diffusion of ortho spin water species and ions in solution) and any intrinsic coupling to the local crystal environment (e.g. due to $^{13}C$ nuclei or interface effects). The evolution of the background system due to self interaction is described by $H_{bg}$, which, in the present methodology, is used to obtain the noise spectra of the various background processes. The following analysis assumes dephasing to be the dominant decoherence channel in the system. Relaxation processes are ignored since all magnetic fields considered are at least 4 orders of magnitude less than the effective crystal field of $D/\gamma_p \sim 0.2$ T, and are hence unable to flip the probe spin over relevant timescales. Phonon excitation in the diamond crystal lead to relaxation times of the order of 100 s [83] and may also be ignored. Before moving onto the numerical simulations, it is useful to consider some important features of the problem.

The decoherence rate of the NV centre is governed by the accumulated phase variance during the control cycle. Maximal dephasing due to a fluctuating field will occur at the cross-over point between the fast (FFL) and slow (SFL) fluctuation regimes [84]. A measure of this cross-over point is the dimensionless ratio $\Theta \equiv f_e/\gamma_p \sigma_B$, where $\tau_e = 1/f_e$ is the correlation time of the fluctuating signal, with cross-over at $\Theta \sim 1$. The field standard deviation $\sigma_B^{ic}$ due to the random nuclear spin of ions and bound water molecules moving in an ion channel (ic) can be estimated as:

$$\sigma_B^{ic} \sim \frac{\mu_0}{4\pi} \frac{1}{h_p^3} \sqrt{N_{ion}\mu_{ion}^2 + N_{H_2O}\mu_{H_2O}^2} . \quad (2)$$

The fluctuation strength of the ion channel magnetic field, $\sigma_B^{ic}$, is plotted in FIG. 9(b) as a function of the probe stand-off distance, $h_p$. Ion flux rates are of the order of $\sim 5 \times 10^{-4}$ ions $ns^{-1}nm^{-2}$ [98], giving an effective dipole field fluctuation rate of $f_e \sim 3 \times 10^4$ Hz. For probe-channel separations of 2-8 nm, values of Θ range from 0.4 to 40 [FIG. 9(c)]. Thus, the ion channel flow hovers near the cross-over point, with an induced dephasing rate of $\Gamma_{ic} \sim 10^4$-$10^5$ Hz.

Considering the dephasing effects of the various sources of background magnetic fields, the first source of background noise is the fluctuating magnetic field arising from the motion of the water molecules and ions throughout the aqueous solution. Due to the nuclear spins of the hydrogen atoms, liquid water consists of a mixture of spin neutral (para) and spin-1 (ortho) molecules. The equilibrium ratio of ortho to para molecules (OP ratio) is 3:1 [99], making 75% of water molecules magnetically active. In biological conditions, dissolved ions occur in concentrations 2-3 orders of magnitude below this and are ignored here (they are important however for calculations of the induced Stark shift, see below). The RMS strength of the field due to the aqueous solution is $$\sigma_B^{H_2O} \sim g_H \mu_N \frac{\mu_0}{2\pi} \sqrt{n_{H_2O} \frac{\pi}{h_p^3}} . \quad (3)$$

Figure 9:
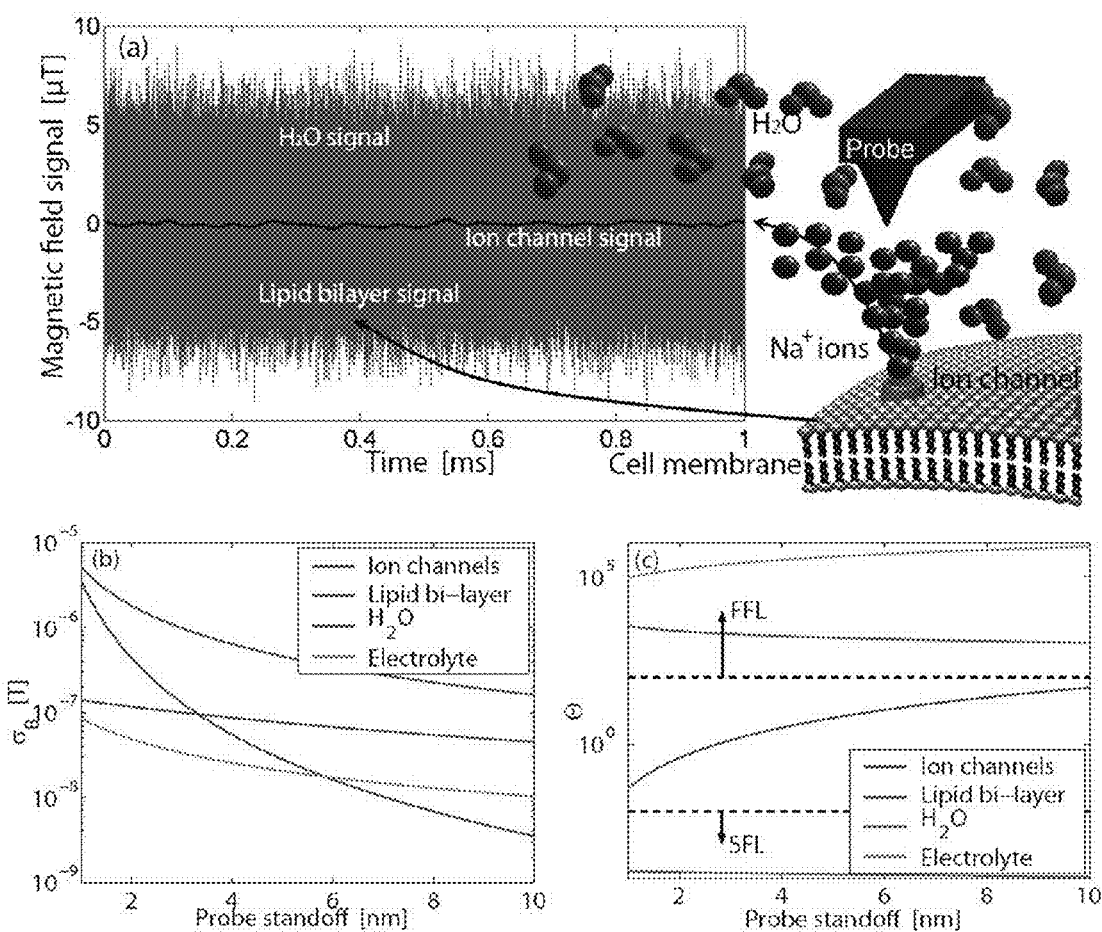
FIG. 9(a) is a two dimensional plot showing typical magnetic field signals from water, ion channel and lipid bilayer sources at a probe standoff of 4 nm over a 1 ms timescale.
FIG. 9(b) is a two dimensional plot showing a comparison of $\sigma_B$ for various sources of magnetic fields against probe standoff distance.
FIG. 9(c) is a two dimensional plot showing a fluctuation regime, $\Theta=f_c/\gamma_p\sigma_B$, for magnetic field sources vs probe standoff (Rapidly fluctuating fields ($\Theta \gg 1$) are said to be in the fast-fluctuating limit (FFL). Slowly fluctuating fields ($\Theta \ll 1$) are in the slow fluctuation limit (SFL). The ion channel signal exists in the $\Theta \sim 1$ regime, and therefore has an optimal dephasing effect on the NV probe.

This magnetic field is therefore 1-2 orders of magnitude stronger than the field from the ion channel [FIG. 9(a,b)]. The fluctuation rate of the aqueous environment is dependent on the self diffusion rate of the water molecules. Using $D_{H_2O} = 3 \times 10^{-9}$ $m^2 s^{-1}$, the fluctuation rate is $f_e^{H_2O} \sim D_{H_2O}/(2h_p)^2$. This places the magnetic field due to the aqueous solution in the fast-fluctuation regime, with $\Theta_{H_2O} \sim 10^3$-$10^4$ [FIG. 9(b)], giving a comparatively slow dephasing rate of $\Gamma_{H_2O} \sim f_e^{H_2O} \Theta_{H_2O}^{-2} \sim 100$ Hz 100 Hz and corresponding dephasing envelope $D_{H_2O} = e^{-\Gamma_{H_2O} t}$.

An additional source of background dephasing is the lipid molecules comprising the cell membrane. Assuming magnetic contributions from hydrogen nuclei in the lipid molecules, lateral diffusion in the cell membrane gives rise to a fluctuating B-field, with a characteristic frequency related to the diffusion rate. Atomic hydrogen densities in the membrane are $n_H \sim 3 \times 10^{28}$ m$^{-3}$. At room temperature, the populations of the spin states of hydrogen will be equal, thus the RMS field strength is given by $$\sigma_B^L \sim g_H \mu_N \frac{\mu_0}{8\pi} \sqrt{n \frac{5\pi}{4 h_p^3}}. \tag{4}$$

The strength of the fluctuating field due to the lipid bilayer is of the order of $10^{-7}$ T [FIG. 9(a)]. The Diffusion constant for lateral Brownian motion of lipid molecules in lipid bilayers is $D_L = 2 \times 10^{-15}$ m$^2$s$^{-1}$ [98], giving a fluctuation frequency of $f_e^L \sim 125$ Hz and $\Theta_L \sim 10^{-4}$ [FIG. 9(d)]. At this frequency, any quasi-static field effects will be predominantly suppressed by the spin-echo refocusing. The leading-order (gradient-channel) dephasing rate is given by [84], $$\Gamma_L \sim \frac{1}{2\sqrt{2\sqrt{2}}} \Theta_L^{-1/2} f_e^L + O(\Theta_L^{-1/3} f_e^L), \tag{5}$$

giving rise to dephasing rates of the order $\Gamma_L \sim 100$ Hz, with corresponding dephasing envelope $D_L(t) = e^{-\Gamma_L^4 t^4}$.

The electric fields associated with the dissolved ions also interact with the NV centre via the ground state Stark effect. The coefficient for the frequency shift as a function of the electric field applied along the dominant (z) axis is given by $R_{3D} = 3.5 \times 10^{-3}$ HzmV$^{-1}$ [98]. Fluctuations in the electric field may be related to an effective magnetic field via $B_z^{\mathit{eff}} = R_{3D} E_z / \gamma_p$, which may be used in an analysis similar to that above. An analysis using Debye-Hückel theory [102] shows charge fluctuations of an ionic solutions in a spherical region $\Lambda$ of radius R behave as $$\langle Q_\Lambda^2 \rangle = D_E k_B T(1 + \kappa R) e^{-\kappa R} \left[ R \cosh(\kappa R) - \frac{\sinh(\kappa R)}{\kappa} \right], \tag{6}$$

where $D_E$ is the diffusion coefficient of the electrolyte, and $\kappa$ is the inverse Debye length $(l_D)$; $l_D = 1/\kappa = 1.3$ nm for biological conditions. Whilst this analysis applies to a region $\Lambda$ embedded in an infinite bulk electrolyte system, simulation results discussed below show very good agreement when applied to the system considered here. Eq. 6 is used to obtain the electric field variance, $\sigma_E = \sqrt{\langle E^2 \rangle - \langle E \rangle^2}$, as a function of $h_p$. Relaxation times for electric field fluctuations are $\tau_e^E = \epsilon \epsilon_0 \rho_E$ [103], where $\rho_E$ is the resistivity of the electrolyte, giving $f_e^E \sim 1/\tau_e^E = 1.4 \times 10^9$ Hz under biological conditions. Given the relatively low strength [FIG. 9(a)] and short relaxation time of the effective Stark induced magnetic field fluctuations ($\Theta : 10^5$) [FIG. 9(b)], it is expected that the charge fluctuations associated with ions in solution has little effect on the evolution of the probe.

Figure 10:
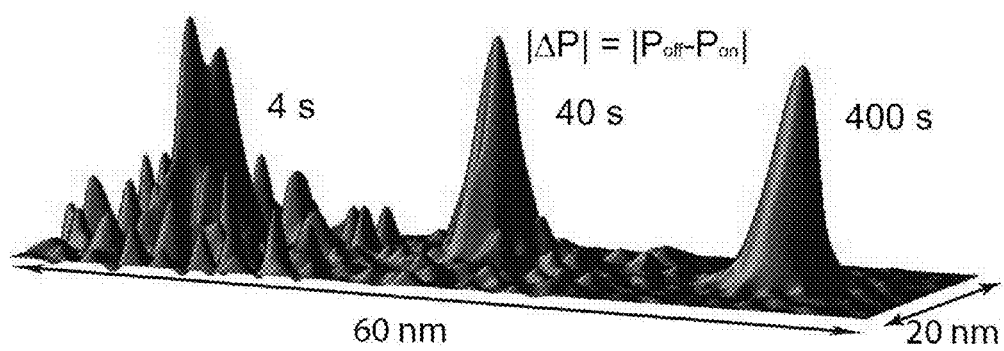
FIG. 10 is three dimensional plots showing spatial information corresponding to the ion channel as a dephasing source (Relative population differences are plotted for pixel dwell times of 10, 100 and 1000 ms, from left to right respectively. Corresponding image acquisition times are 4, 40 and 400 s)
Figure 11:
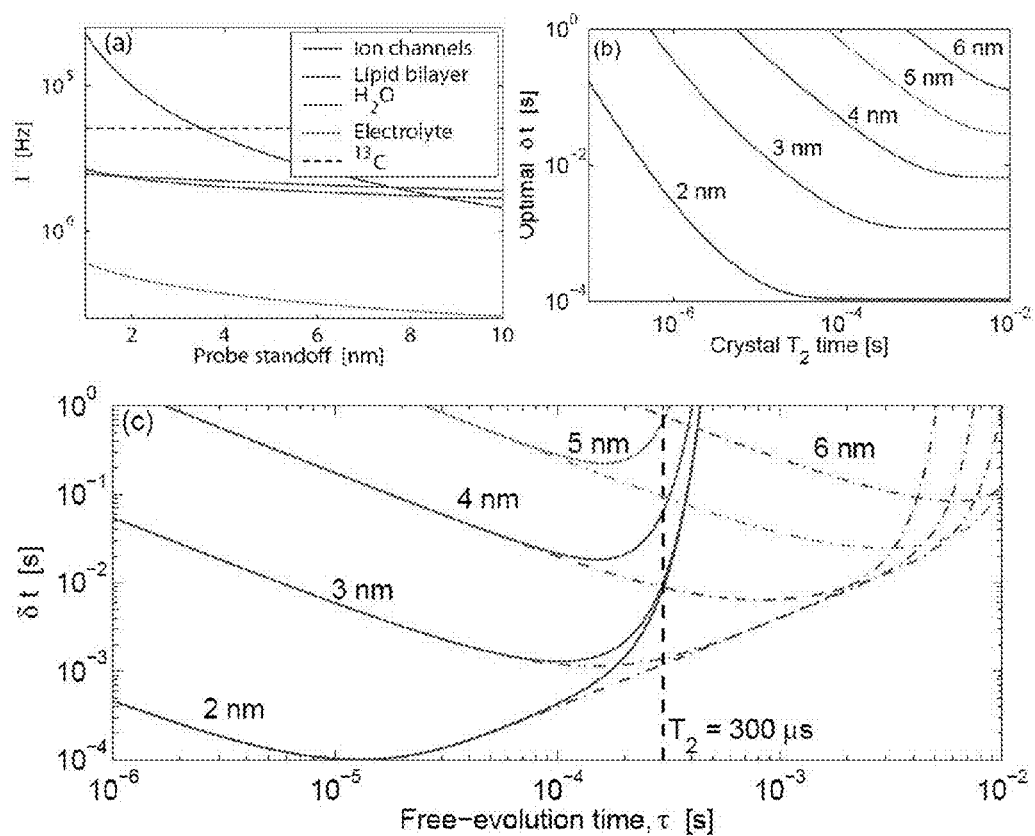
FIG. 11(a) is a two dimensional plot showing dephasing rates due to the sources of magnetic field plotted as a function of probe standoff, $h_p$.
FIG. 11(b) is a two dimensional plot showing optimum temporal resolution as a function of crystal $T_2$ times for $h_p$=2-6 nm.
FIG. 11(c) is a two dimensional plot showing temporal resolution as a function of interrogation time, $\tau$, for separations of 2-6 nm and $T_2$=300 µs (Dashed lines show expected improvements from much longer $T_2$ times, $T_2 \gg \tau$)
Figure 12:
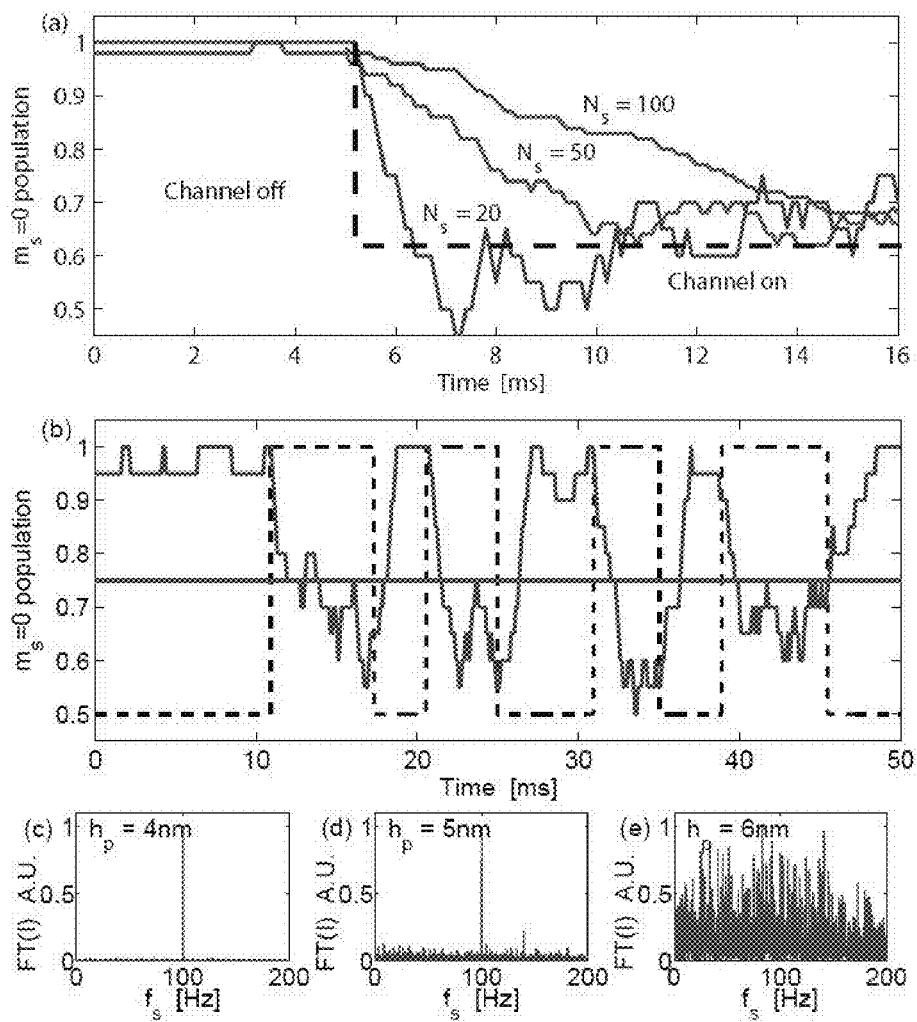
FIG. 12 (c)-(e) are two dimensional plots showing Fourier transforms of measurement records for stand-offs of 4, 5 and 6 nm respectively (Switching dynamics are clearly resolvable for $h_p$<6 nm, beyond which there is little contrast between decoherence due to the ion channel signal and the background)

The problem of non-invasively resolving the location of a sodium ion channel in a lipid bilayer membrane is now considered. When the channel is closed, the dephasing is the result of the background activity, and is defined by $D_{\mathit{off}} = D_{H_2O} D_L D_E D_{13C}$. When the channel is open, the dephasing envelope is defined by $D_{on} = D_{\mathit{off}} D_{ic}$. Maximum contrast will be achieved by optimising the spin-echo interrogation time, $\tau$, to ensure $D_{\mathit{off}} - D_{on}$ is maximal. Thus for $\tau \approx T_2/2$ in the vicinity of an open channel we expect an ensemble ground state population of $$P_{on}\left(\frac{T_2}{2}\right) = \frac{1}{2}\left[1 + D_{on}\left(\frac{T_2}{2}\right)\right] = 0.61, \text{ and}$$

$$P_{\mathit{off}}\left(\frac{T_2}{2}\right) = \frac{1}{2}\left[1 + D_{\mathit{off}}\left(\frac{T_2}{2}\right)\right] = 0.93$$

otherwise. By scanning over an open ion channel and monitoring the probe via repeated measurements of the spin state, a population ensemble may be built up for each lateral point in the sample. The signal to noise ratio improves with the dwell times at each point. FIG. 10 shows simulated scans of a sodium ion channel with corresponding image acquisition times of 4, 40 and 400 s. It should be noted here that the spatial resolution available with this technique is beyond that achievable by magnetic field measurements alone, since for large $\Theta$, $\Delta P \propto B^2 \propto h_p^{-6}$.

Similar techniques are employed to temporally resolve a sodium ion channel switch-on event. By monitoring a single point, a measurement record sequence, $I$, may be built up. In an experimental situation, the frequency with which measurements may be performed has an upper limit of $f_m = (\tau + \tau_m + \tau_{2\pi})^{-1}$, where $\tau_m \approx 900$ ns is the time required for photon collection, and $\tau_{2\pi}$ is the time required for all 3 microwave pulses. A potential trade-off exists between the increased dephasing due to longer interrogation times and the corresponding reduction in measurement frequency.

Interrogation times are ultimately limited by the intrinsic $T_2$ time of the crystal. A second trade-off exists between the variance of a given set of $N_\tau$ consecutive measurements and the temporal resolution of the probe. For the monitoring of a switching event, the spin state population may be inferred with increased confidence by performing a running average over a larger number of data points, $N_\tau$. However increasing $N_\tau$ will lead to a longer time lag before a definitive result is obtained. The uncertainty in the ion channel state goes as $\delta P \sim (\sqrt{N_\tau})^{-1}$, where $N_\tau$ is the number of points included in the dynamic averaging. We must take sufficient $N_\tau$ to ensure that $\delta P < \Delta P(\tau, h_p, T_2) = P_{\mathit{off}} - P_{on}$. The temporal resolution depends on the width of the dynamic average and is given by $\delta t \sim N_\tau (\tau + \tau_m)$, giving the relationship $$\delta t = \frac{\tau + \tau_m}{\delta P^2} > \frac{\tau + \tau_m}{[\Delta P(\tau, h_p, T_2)]^2}. \tag{7}$$

It is desirable to minimise this function with respect to $\tau$ for a given stand-off ($h_p$) and crystal $T_2$ time.

In reality, not all crystals are manufactured with equal $T_2$ times. An important question is therefore, for a given $T_2$, what is the best achievable temporal resolution? FIG. 11(b) shows the optimal temporal resolution as a function of $T_2$. It can be seen that $\delta t$ improves monotonically with $T_2$ until $T_2$ exceeds the dephasing time due to the fluctuating background fields [FIG. 11(a)]. Beyond this point no advantage is found from extending $T_2$.

A plot of $\delta t$ as a function of $\tau$ is shown in FIG. 11(c) for standoffs of 2-6 nm. Solid lines depict the resolution that may be achieved with $T_2 = 300$ µs. Dashed lines represent the resolution that may be achieved by extending $T_2$ beyond the dephasing times of background fields. We see that $\delta t$ diverges as $\tau \to T_2$, and is optimal for $\tau \to 1/\Gamma_{ic}$.

As an example of monitoring of ion channel behaviour, consider a crystal with a $T_2$ time of 300 µs at a standoff of 3 nm. FIG. 11(c) tells us that an optimal temporal resolution of δt~1.1 ms may be achieved by choosing T~100 µs. This in turn suggests an optimal running average will employ $N_\tau = \delta t (\tau + \tau_m)^{-1} \approx 11$ data points. FIG. 12(a) shows a simulated detection of a sodium ion channel switch-on event using $N_\tau$=20.50 and 100 points. The effect of increasing $N_\tau$ is shown to give poorer temporal resolution but also produces a lower variance in the signal. This may be necessary if there is little contrast between $P_{off}$ and $P_{on}$. Conversely, decreasing $N_\tau$ results in an improvement to the temporal resolution but leads to a larger signal variation.

An ion channel switching between states after an average waiting time of 5 ms (200 Hz) [FIG. 12(b)] is now considered. To ensure the condition δP<ΔP is satisfied, an analysis is performed using $N_\tau$=20, giving a resolution of δt≈2 ms. The blue curve shows the response of the NV population to changes in the ion channel state. Fourier transforms of the measurement record, F(l), are shown in FIG. 12(c)-(e). The switching dynamics are clearly resolvable for heights less than 6 nm. The dominant spectral frequency is 100 Hz which is half the 200 Hz switching rate as expected. Beyond 6 nm, the contrast between $P_{off}$ and $P_{on}$ is too small to be resolvable due to the $T_2$ limited temporal resolution, as given in FIG. 11(b). This may be improved via the manufacturing of nanocrystals with improved $T_2$ times, allowing for longer interrogation times [dashed curves, FIG. 11(c)].

With regard to scale-up to a wide field imaging capability, beyond the obvious extrinsic scaling of the number of single channel detection elements (in conjunction with micro-confocal arrays), an intrinsic scale-up strategy using many NV centres in a bulk diamond probe, with photons collected in a pixel arrangement, is considered. Since the activity of adjacent ion channels is correlated by the µm scale activity of the membrane, the fluorescence of adjacent NV centres will likewise be correlated, thus wide field detection will occur via a fluorescence contrast across the pixel. Implementation of this scheme involves a random distribution of NV centres in a bulk diamond crystal. The highest NV densities reported in bulk crystals with no neutrally charged $NV^0$ defects are $2.8 \times 10^{24}$ $m^{-3}$ [104], giving typical NV-NV couplings of <10 MHz, which are too weak to induce NV spin-flips. It is desirable to seek a balance between increased population contrast and increased dephasing rates due to higher NV densities.

For ion channel operation correlated across each pixel, the total population contrast ΔΦ between off and on states is obtained by averaging the local NV state population change $\Delta\Phi(\tau) = P_{off}(\vec{r}_i, \vec{r}_c, \tau) - P_{on}(\vec{r}_i, \vec{r}_c, \tau)$ over all NV positions $\vec{r}_i$ and orientations; and ion channel positions $\vec{r}_c$ (and species); and maximizing with respect to τ. As an example, consider a crystal with an NV density of $10^{24}$ $m^{-3}$ whose surface is brought within 3 nm of the cell membrane containing an sodium and potassium ion channel densities of ~$2 \times 10^{15}$ $m^{-2}$ [105]. Ion channel activity is expected to be correlated across pixel areas of 1 µm×1 µm, so the population contrast between off and on states is ΔΦ≈500. This directly translates into an improvement in the temporal resolution by a factor of 1000, opening up the potential for single-shot measurements of ion channel activity across each pixel.

An analysis of the quantum dynamics of a NV diamond probe in the cell-membrane environment has been carried out so as to determined the theoretical sensitivity for the detection, monitoring and imaging of single ion channel function through quantum decoherence. Using current demonstrated technology a temporal resolution in the 1-10 ms range is possible, with spatial resolution at the nanometer level. With the scope for scale-up and novel scanning modes, this fundamentally new detection mode has the potential to revolutionize the characterization of ion channel action, and possibly other membrane proteins, with important implications for molecular biology and drug discovery.

Referring now to FIG. 13 to 17, apparatus and methods for monitoring a nanoscopic property of a sample in accordance with another specific embodiment of the present invention are described.

This embodiment of the method in accordance with the present invention also aims to use decoherence based imaging to detect random magnetic field fluctuations as a result of their impact on the quantum evolution of a quantum probe system. Because many interesting biological processes would be characterized by random field variations and these may average out to zero, the detection of the average field using DC magnetometry would not be suitable. AC detection is more sensitive but relies on precise control of the sample's evolution. The decoherence rate can be an effect measure of such random zero mean fluctuations.

Figure 13:
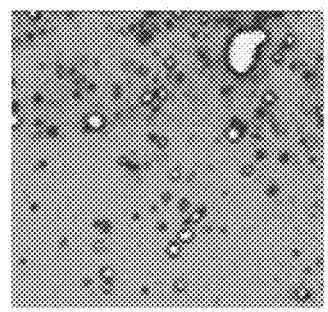
FIG. 13 (a) shows a schematic set-up of components for monitoring a property of a sample in accordance with a specific embodiment of the present invention.
Figure 13:
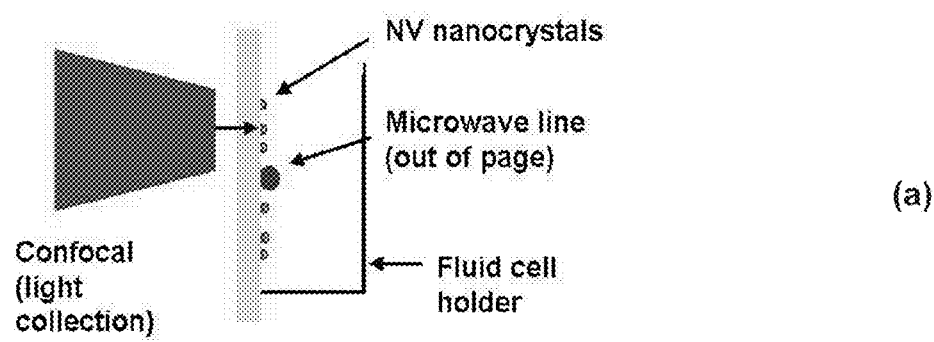

FIG. 13 (a) shows a confocal scanning system that is combined with GHz microwave control and is arranged to introduce, in a controlled manner, fluctuating magnetic fields in an aqueous environment.

The following will initially describe establishing a control sample of non-immersed NV-centre in a diamond nanocrystal in air. A region of the sample which has diamond nanocrystals of size roughly 50 nm deposited (see FIG. 13 (b)) is scanned and those crystals containing a single NV centre are identified through anti-bunching. Optically detected magnetic resonance (ODMR) was conducted by scanning the microwave frequency and watching for the dip in fluorescence corresponding to exciting the magnetic levels of the particular NV centre under observation. From the ODMR the resonance microwave frequency is determined. This resonance frequency microwave signal is applied to the NV centre in a Rabi experiment where the NV fluorescence is monitored as a function of time and the coherence oscillations between the two magnetic levels observed directly. For this microwave power the Rabi period (time between oscillations) is determined.

Figure 14:
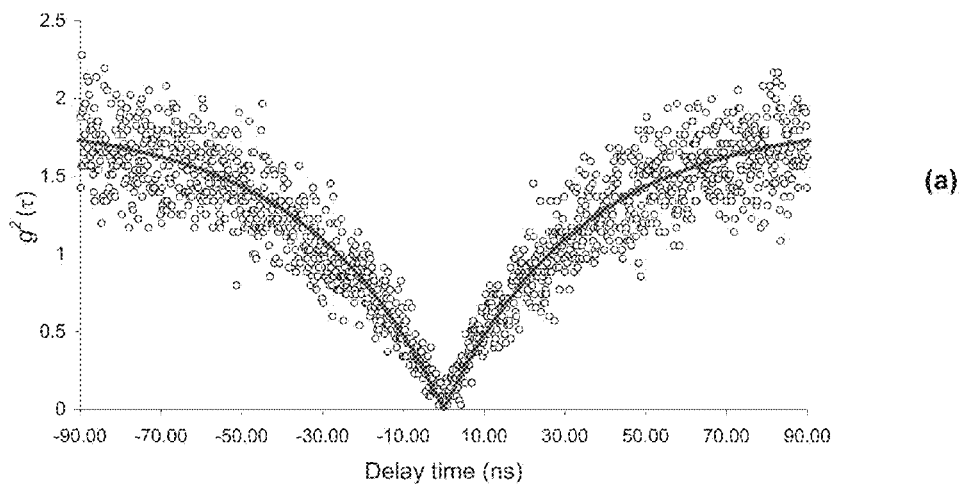
FIG. 14 shows a measurement indicating quantum decoherece (arbitrary units) in accordance with a specific embodiment of the present invention.
Figure 14:
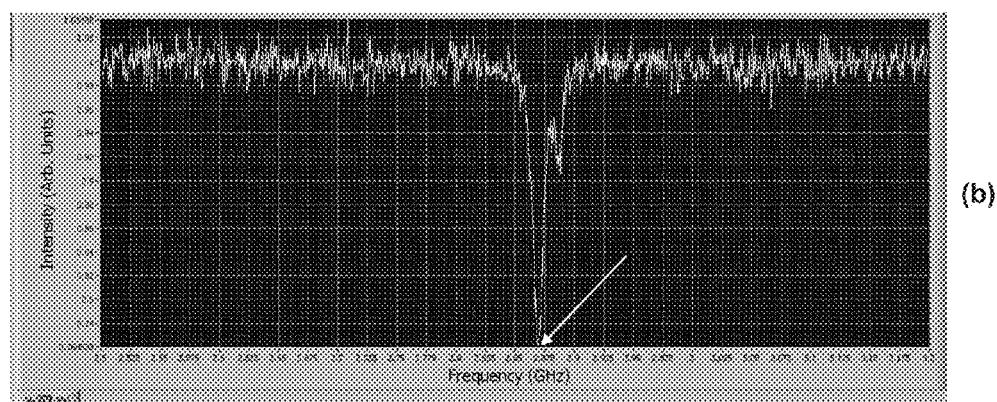
Figure 14:
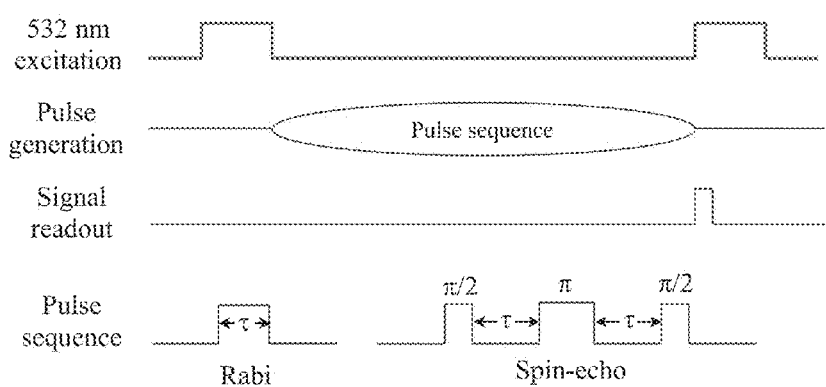

From this Rabi period the duration of control pulses is determined to carry out the spin-echo measurements of the decoherence. As described previously, in these measurements the decoherence time corresponds to how the spin-echo signal determined by fluorescence decays as a function of time. FIG. 14 shows the Rabi data taken from a NV centre in air. The envelope decay corresponds to decoherence processes in the immediate environment.

Figure 15:
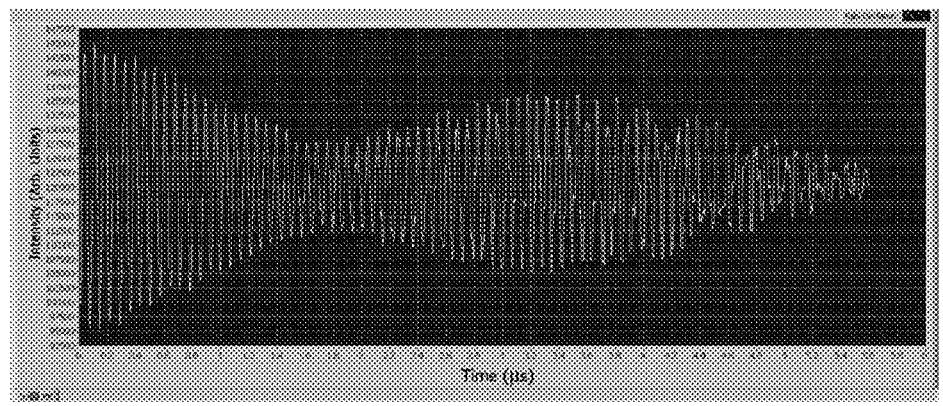
FIG. 15 shows a spin-echo intensity (arbitrary units) as a function of time indicative of quantum decoherence in both air and water environments.
Figure 15:
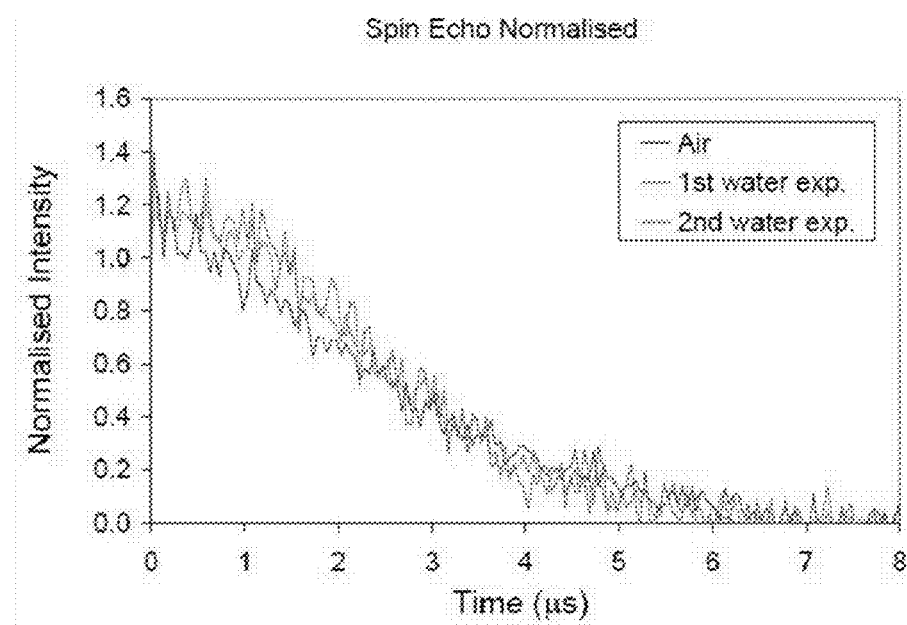

FIG. 15 shows spin echo results illustrating the decay in coherence as a function of time before and after immersion in pure water. This plot in FIG. 15 indicates how the quantum coherence of a particular NV centre changes over several microseconds for various immersion conditions. Where the curve flattens out at (6 microseconds in this case) quantum decoherence has essentially been lost due to the environmental magnetic fluctuations around the NV (crystal and beyond).

While there are slight differences, after the Rabi pulse has been tuned for the particular immersion condition, air and water have a similar effect. This is an important control experiment that shows that immersion in water (required for biology) does not significantly affect the decoherence time of the NV centre, as theory predicts.

Figure 16:
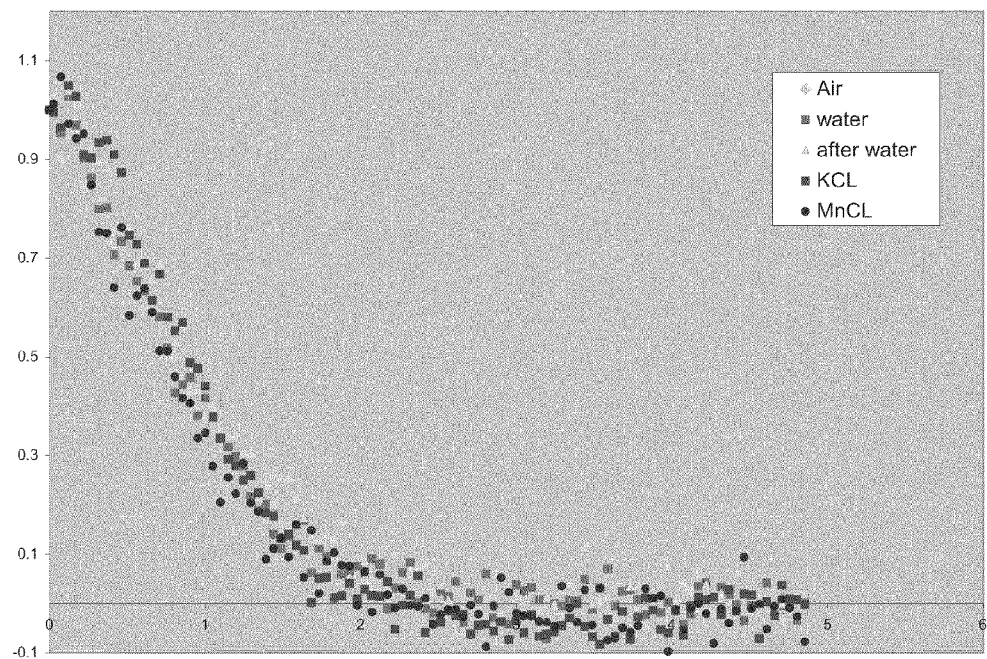
FIGS. 16 and 17 show spin-echo intensities (arbitrary units) as a function of time indicative of quantum decoherence.
Figure 17:
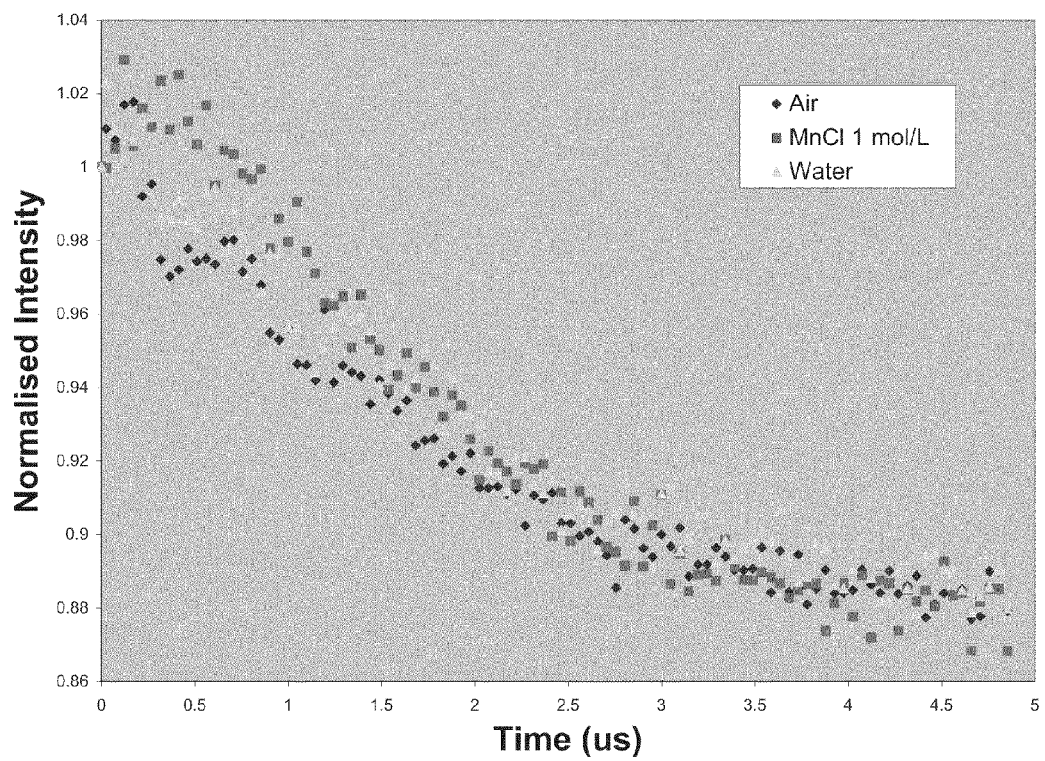

FIG. 16 shows measurements illustrating loss of quantum coherence as a function of time (arbitrary) units for NV-centres immersed in various fluids. FIG. 17 shows measurements illustrating loss of quantum coherence as a function of time (arbitrary units) for a high concentration $Mn^{2+}$ ions compared to controls.

Figure 18:
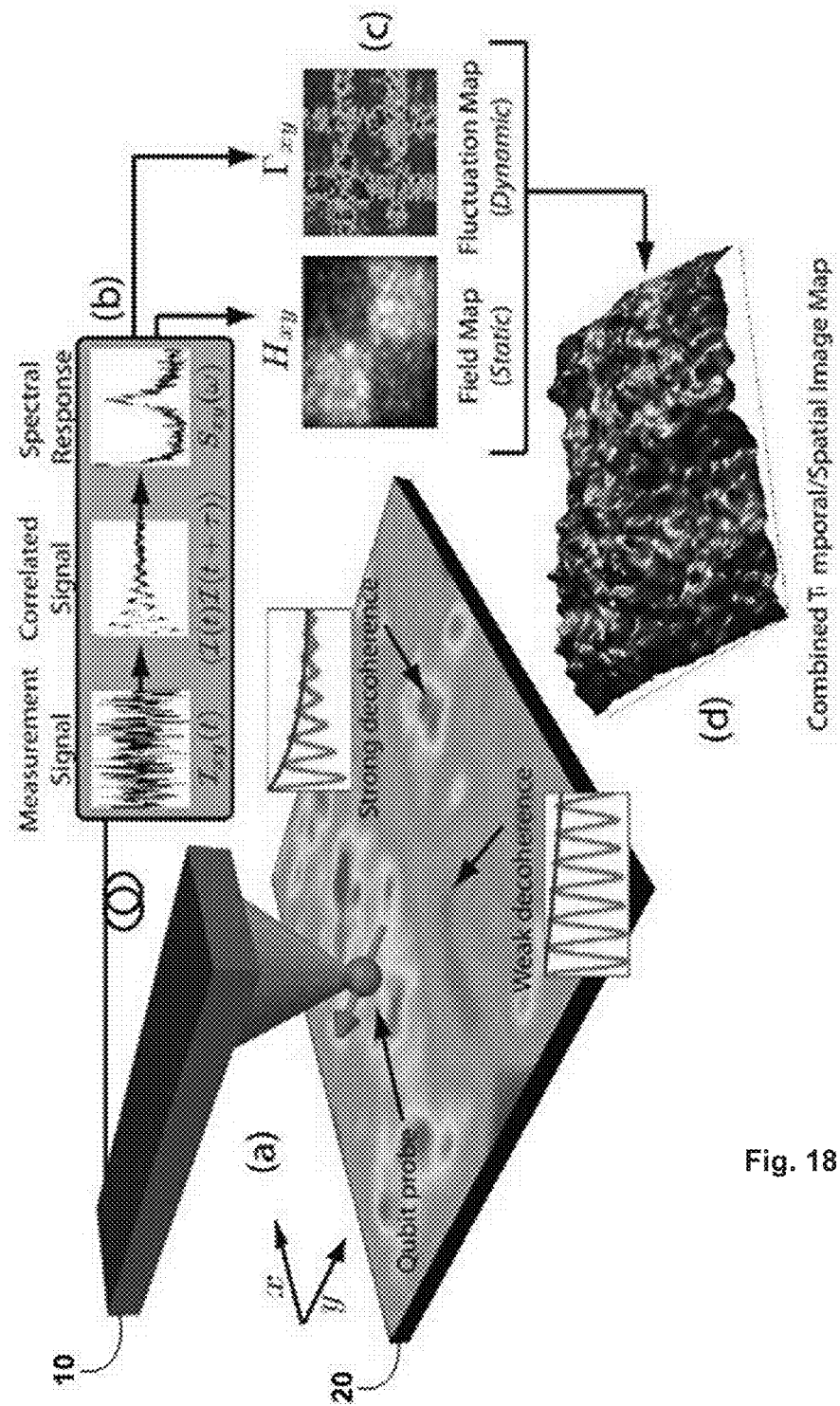
FIG. 18(a) illustrates an apparatus for monitoring a property in accordance with a specific embodiment of the present invention.
FIG. 18(b) is a series of three signal images, representing respectively a measurement signal, a Correlated signal and a Spectral response.
FIG. 18(c) is a pair of images of the surface, one a static field map and the other a dynamic fluctuation map.
FIG. 18(d) is a 3-D terrain image derived from combination of the static field map and the dynamic fluctuation map of FIG. 18(c)

Referring now to FIG. 18(a) a method and an apparatus for monitoring a property in accordance with a further specific embodiment of the present invention is now described. The apparatus comprises a quantum probe 10, located at position (x,y), suspended a distance $h_p$ above the sample. The quantum probe 10 is itself a two-state system (a qubit), based on charge or spin degrees of freedom, attached to the end of a cantilever probe 10. The quantum probe qubit is scanned across the sample while its quantum state is (weakly) monitored, providing a measurement record $I_{xy}(t)$.

At each point (x,y) a measurement $I_{xy}(t)$ is obtained and recorded, see FIG. 18(b) "Measurement signal". This measurement record is then time correlated, see FIG. 18(b) "Correlated signal", and the spectral response $S_{xy}(\omega)$ is computed from the correlated signal, see FIG. 18(b) "Spectral response".

From the spectral response $S_{xy}(\omega)$ a measurement of the effective qubit Hamiltonian $H_{xy}$ (static magnetometer or electrometer) field map is made, and a decoherence rate $\Gamma_{xy}$ map as a function of probe position is obtained, see FIG. 12(c).

If the components of the Hamiltonian were plotted as a function of position across the sample ($H_{xy}$), the probe would be acting as a sensitive electrometer or magnetometer (depending on the type of qubit), as given in the $H_{xy}$ example, see FIG. 18(c). The use of qubits, or other few state quantum systems, as sensitive magnetometers (or electrometers) has previously been discussed[1-4] as the evolution of a qubit depends very precisely on its electromagnetic environment, providing the possibility of quantum limited detection.

Complete analysis of the probe evolution allows the decoherence channel(s) to be extracted, giving information about the strength, direction and character of the dynamics of the environment, as well as the induced static field.

The sample in this case consists of fluctuators with a non uniform distribution in both spatial density and fluctuation rate. The decoherence rate $\Gamma_{xy}$ map (or Fluctuation map), shown in FIG. 18(c), reveals new information about the fluctuator frequency distribution in the sample which was not apparent in the static field map (electrometer/magnetometer image).

Combining the decoherence rate $\Gamma_{xy}$ map together with the static field map $H_{xy}$ provides a direct window into the distribution and character of the sources of field fluctuations in both space and time, see FIG. 18(d). This image of a 3-Dimensional surface represents the combined temporal and spatial information, and the height of the peaks indicates the strength of the field, whereas colouration can be used to represent the effective decoherence rate (no colour can be seen in the black and white images presented only shading).

Monitoring both the position dependent probe Hamiltonian and decoherence channels allows one to use the scanning quantum system as both a magnetometer/electrometer and as a probe of the decoherence environment simultaneously.

Thanks (in part) to the ongoing work to construct controllable quantum devices[5], a number of techniques have been developed to measure the state or evolution characteristics of a quantum system. These include techniques to reconstruct an arbitrary quantum state or process[5,6], quantum channel[5,7] and the Hamiltonian governing a few state quantum system[8-13] or even spin echo techniques[14] from magnetic resonance. We have focused on the technique of Hamiltonian characterization[8-10] but other techniques can be similarly applied.

Quantitative Model

To make the embodiments of the present invention quantitative, we introduce a simple model for weak continuous measurement[15] which captures all of the essential physics[50]. We assume the measurement of the qubit can be modeled as a inefficient (or weak) POVM (Positive Operator Valued Measure) in the $\sigma_z$ basis. The density matrix after measurement, $\rho'$, is given by $$\rho' = \frac{A_{\pm} \rho A_{\pm}^{\dagger}}{Tr[A_{\pm}^{\dagger} A_{\pm} \rho]} \qquad (8)$$

for a measurement operator $$A_{\pm} = \frac{1}{\sqrt{2}} \left( \sqrt{1 \pm \kappa} |0\rangle\langle 0| + \sqrt{1 \mp \kappa} |1\rangle\langle 1| \right) \qquad (9)$$

with some measurement strength $\kappa$. The measurement process consists of repeated weak POVM measurements separated by a time interval $\Delta t$, during which time the system undergoes normal evolution. The measurement repetition interval is then a measure of the bandwidth of the detector, $BW = 1/\Delta t$.

The measurement record I(t), is the result, +1 or −1, of a measurement at time t. The steady-state autocorrelation of this measurement signal I(t) is then given by $$\langle I(t)I(t+\tau)\rangle_{ss} = Tr[\sigma_z e^{\mathcal{L}\tau} \sigma_z \rho_{ss}] \qquad (10)$$

via the quantum regression theorem[16,17]. Here $\rho_{ss} = \rho(\infty)$ is the steady state density matrix and is the solution to the density matrix evolution governed by, where H is the qubit Hamiltonian and $\Gamma$ represents the decoherence rate of the system without measurement. The spectrum of the signal is then $$S(\omega) = \mathcal{F}\left[ \frac{\langle I(t)I(l+\tau)\rangle_{ss} - I_{ss}^2}{\langle I(l)I(t)\rangle_{ss} - I_{ss}^2} \right] = \mathcal{F}[\langle \sigma_z(t)\rangle] \qquad (11)$$

Where $\mathcal{F}[\langle \rho_2(t)\rangle]$ is the Fourier transform of the (ensemble averaged) expectation value of the $\sigma_z$ operator. From this response spectrum, we extract the Hamiltonian and decoherence parameters directly[9,10] for each spatial location across the sample.

In the limit of small $\kappa$, this model is equivalent[15] to more complicated master equation models[15,18-21]. Expanding the evolution to first order in both $\kappa$ and $\Delta t$, we can derive an equivalent Lindbladian master equation with an effective $\sigma_z$ decoherence channel of strength $$\Gamma_{meas} = \frac{\kappa^2}{4\Delta t} \qquad (12)$$

which corresponds to the measurement induced decoherence. In general, the measurement strength should be chosen such that this induced decoherence is smaller than both the sample induced decoherence and other intrinsic decoherence sources[51].

We can also calculate the information extracted from the system at each measurement step by looking at the reduction in entropy of the system. Expanding for small $\kappa$, this gives $$\Delta S_E = S_E(\rho) - S_E(\rho') = \frac{\kappa^2}{\log_e(4)} + O(\kappa^3) \qquad (13)$$

as the information obtained (in bits) from a single measurement of an initially mixed state. So, it is clear that we have a trade off. As we increase κ or the bandwidth, the amount of information obtained in a given time interval is increased, Eq. (11), at the expense of greater measurement induced decoherence, Eq. (12).

The spatial resolution of the probe system is ultimately governed by the effective strength of the environmental decoherence as a function of distance. Most decoherence channels (for solid-state qubits) depend, in some way, on the inverse of the separation between qubit and environment. The coupling between a single decoherence (point) source and the probe qubit is, in general, proportional to $1/r^n$, hence the response of the qubit as a function of (x−)position across the sample is given by a exponentiated Lorenztian. The Full Width at Half Maximum (FWHM) of this function gives the spatial resolution, where $h_p$ is the height of the probe above the sample. By inspection, we see an electric dipole induced potential ($1/r^2$) has a FWHM 2hp whereas a magnetic dipolar interaction ($1/r^3$) has slightly better resolution, $\Delta x \approx 1.53 h_p$. The achievable spatial resolution is lower than (for example) Scanning Tunnelling Microscopy (STM) where the electron current is exponentially dependent on the sample-probe separation[22]. The point here is that the information provided by this imaging mode is of a fundamentally different and complementary nature to conventional imaging techniques.

FURTHER EXAMPLES

The following will consider in detail two examples in which the effects of a decohering environment on an example probe are simulated. These examples provide both a straightforward illustration of the power of imaging the sample induced decoherence and a test of the feasibility using current and near future technology.

Example I

Imaging the Distribution of Background Charge Fluctuators

Our first example system comprises an electrostatic qubit interacting with a sample containing background charge fluctuators. This example is of particular interest as background charge fluctuations have been the subject of intense scrutiny due to their relevance to solid-state quantum devices and that they are a good example of a nontrivial environmental bath[23, 24]. In this case, we can probe the spatial and frequency distribution of these fluctuators in a way which is not possible using current microscopy techniques.

For this application, a suitable probe qubit would be any of the myriad of charge based 35 qubit designs such as quantum-dots[25], donors[26] or cooper-pair-box[27-29]. A probe based on a cooper-pair-box (CPB) system provides a particularly good example as CPB qubits are now regularly produced experimentally[30-32] and the bias point of the system can be varied, resulting in a change in the sensitivity to different components of the environmental decoherence[23]. Although, for these devices the ultimate resolution limit is given by the physical size of the device, in which case a quantum dot or even charge donor system may be better.

For generality, this analysis does not assume a particular qubit implementation, modelling the qubit purely as a two-state system which interacts via a field dependent component in its Hamiltonian (see Methods section I below). For this reason, all the dimensions in this example are given in terms of a normalized length scale (L).

We consider a 2D surface which contains background charge fluctuators that we wish to image. We use a simplified model of these fluctuators in the fast fluctuator limit, to illustrate the concepts. (In example II, we will consider a more specific example in the slow fluctuator limit.)

We take the potential felt by the qubit as a simple electrostatic potential due to a charge defect dipole and simulate the effective decoherence field felt by the qubit due to the fluctuator bath (defects in the sample). In FIG. 13(a), we have a fictitious sample 10 containing regions (outlined in white) containing a uniform fluctuator distribution with an area density of 1000 defects per square (all distances are in normalised units). The frequencies of these fluctuators are then assumed to be distributed with a 1/f distribution.

The fluctuators are modeled as point sources but have been enlarged in FIG. 13(a) for clarity. As we have not chosen a particular qubit architecture, the coding of the fluctuator locations (shading) depends on the frequency of the fluctuator, in units of the qubit probe frequency. The region on the left is a calibration region where the fluctuator frequency varies with position in the region. This will illustrate the frequency selective nature of the measurement process. The other regions contain fluctuators with a uniform spatial and 1/f frequency distribution.

The variation of the probe Hamiltonian, $H_{xy}$, due to the presence of background charges is shown in FIG. 13(b). The background charges are taken to be charge dipoles[24,33] coupling to the qubit as $1/r^2$ and the probe is positioned $h_p=0.05$ L above the sample. Initially assuming the fluctuators to be static, the spatial variation in the Hamiltonian coupling term is then a measure of the electric potential induced by the dipoles (a simple electrometer). The state of the fluctuators will not be static (in general) and the total induced field will result from an average over the fluctuator states.

In FIG. 18(c), we calculate the decoherence effect felt by the probe due to the combined effects of all the fluctuators in our fictitious sample. The effective decoherence (normalized) rate felt by the qubit is illustrated as a function of position. The qubit is now sensitive to the 1/f nature of the fluctuator bath, with a relatively small number of fluctuators contributed a large fraction of the decohering effect. The resolution (for this example only) increases by a factor of 1.55, compared to measuring the Hamiltonian, as $\Gamma \propto S(\omega) \propto 1/r^4$. Comparing these images, we see that the decoherence measurement is more sensitive to a select few of the fluctuators whose frequency are closest to the probe energy (as is expected for a 1/f distribution). It is known that, for a 40 1/f bath, a relatively small fraction of the total fluctuators contributed a large amount of the total decoherence[23] but here we see it strikingly depicted in the images.

Figure 19:
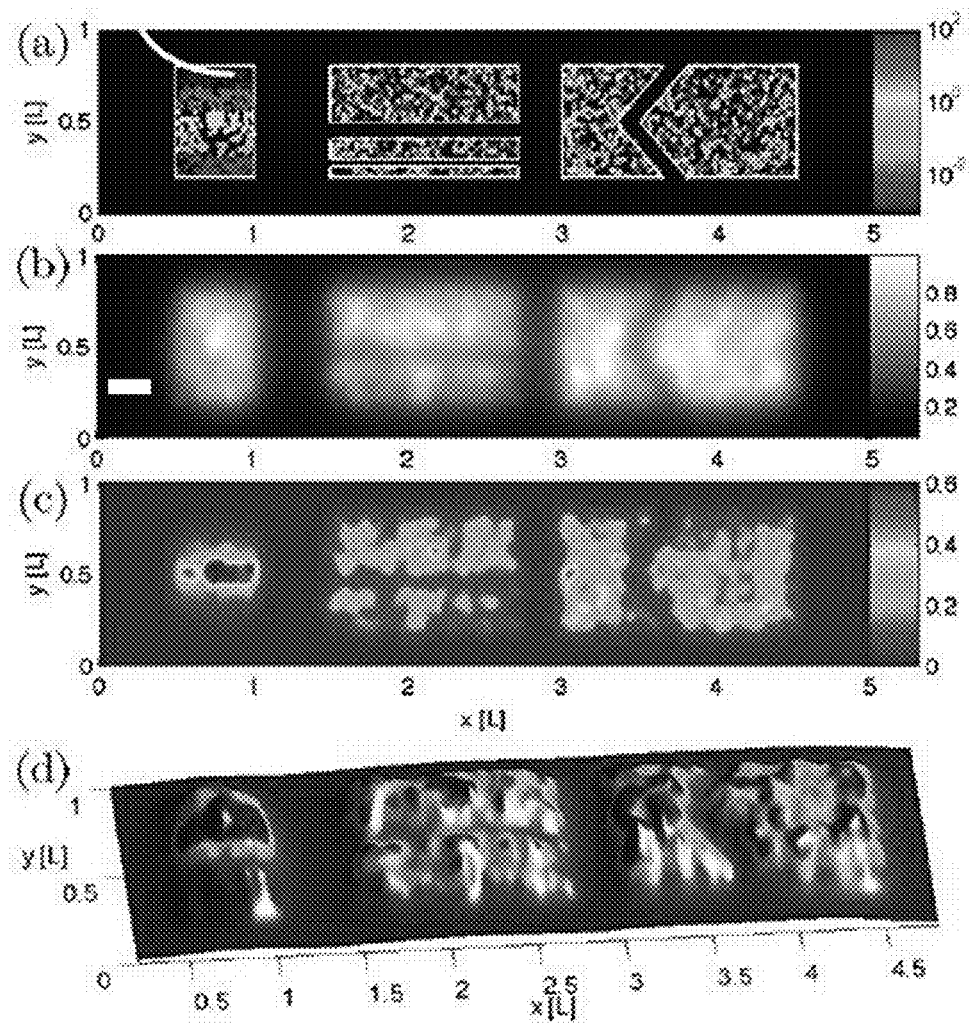
FIG. 19(a) is a series of images of an example sample with uniform distribution of fluctuators (shaded dots) within non-trivial spatial regions (outlined in white)
FIG. 19(b) is a series of images (corresponding to FIG. 19(a)) showing simulated responses of the probe Hamiltonian interacting with a uniformly distributed bath of charge dipoles, with $h_p$=0.05 L.
FIG. 19(c) is a series of images (corresponding to FIG. 19(b)) showing the (normalised) Hamiltonian component induced by the background charges plotted as the grey scale.
FIG. 19(d) is a series of images where the corresponding images of FIGS. 19(b) and (c) have been combined using the value of (b) for the height and (c) for the colour.

To further demonstrate the utility of mapping both Hamiltonian and decoherence components simultaneously, FIG. 19(d) is a combined plot of both FIG. 19(b) and FIG. 19(c). The vertical scale of the 'mountain range' of FIG. 19(d) corresponds to the varying electric potential across the sample. Some 'mountains' are fluctuators with frequency close to the qubit transition frequency while other 'mountains' corresponds to far off resonant 45 fluctuators. (Although it is not possible to show this in these drawings, colour shading can be used to differentiate theses two different kinds of peaks). In this case, the effective field (static) is a surface plot with shading corresponding to the decoherence rate (dynamics). The frequency selective nature of the image is apparent, and fluctuators closest to the probe in energy contribute the most decoherence signal, which are seen as peaks, but other peaks are to due to fluctuators which do not strongly decohere the qubit.

In principle, the frequency sensitivity of the qubit can be tuned to probe different components of the decoherence and obtain more information about its characteristics.

Example II

Imaging the Position and Spin State of Ferritin Molecules

The following will consider the imaging of (bio)molecules with large uncompensated spin, such as 15 Horse-spleen Ferritin[34,35] or $Fe_{836}$. Here, the point is neither to image an individual spin[37] or image the location of the molecules[22,38,39] as both can be done with existing technology. We show that qubit probe imaging can both map the location of the spins and probe their magnetic dynamics.

The decoherence introduced at the probe qubit will be a function of both the interaction strength and the flipping rate of the sample spins. As we are considering large sample spins in a static magnetic field at low temperature, we will assume that the flipping rate is slow on the scale of the probe Hamiltonian. This means that the spectral response of the qubit is split, with the separation between the peaks giving the effective difference in the Hamiltonian between the two sample spin states.

Figure 20:
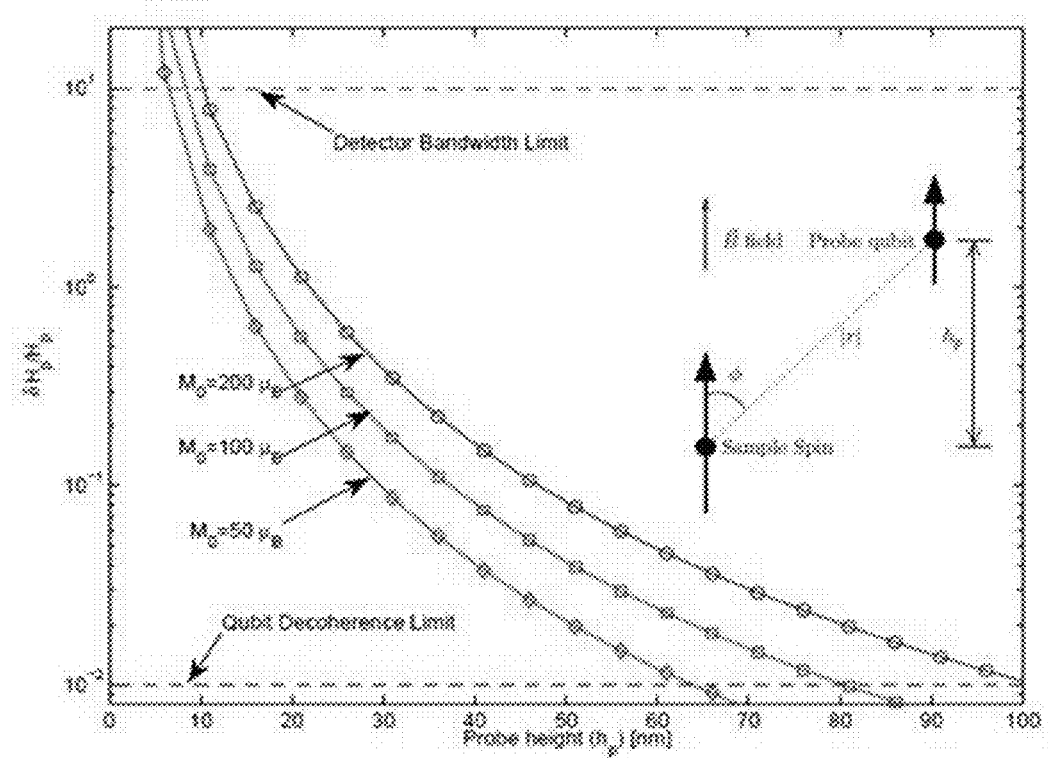
FIG. 20 is a graph showing the variation in strength of the maximum signal ($\phi$=0) as a function of probe height for different sized spins, in this case ferritin molecules.

We compute the coupling strength between the spins, given the simplified magnetic dipolar model, as illustrated in the insert of FIG. 20. The ability to resolve the induced coupling is ultimately limited by the total effective decoherence rate of the qubit. The ratio of the peaks also gives a measure of the relative spin populations, which in turn relates to the effective temperature and/or flipping mechanism.

In FIG. 20, using experimentally realistic parameters for both the probe qubit and the sample spin, we plot the response of the system as it passes over the spin. We use a 35 Nitrogen-Vacancy centre in diamond as our probe spin, as this has been shown to be a controllable, well isolated spin system which displays stable quantum coherent properties up to room temperature[40-47]. We then couple this probe to a bulk spin of order $M_0 = 50-200\mu_B$ and include the effects of intrinsic decoherence and finite measurement bandwidth.

An alternative probe qubit system would be a microSQUID or flux qubit[2,3,27]. This allows easier coupling to the measurement channel, higher precision spectral response measurements and uses demonstrated technology, but it is not a point-source probe. These devices also have the advantage of a tunable working point, which allows adjustment of the qubit's sensitivity to decoherence.

For our example, we use known system parameters for an NV centre driven by a microwave loop and readout via a laser probe measurement[48]. We take the Rabi frequency of the qubit to be 10 MHz, the measurement bandwidth BW=100 MHz but not necessarily 'strong' and the intrinsic decoherence rate is approximately 100 times slower than the Rabi frequency. The measurement strength κ is chosen such that the measurement induced decoherence is weaker than the intrinsic decoherence, for a given detector bandwidth.

FIG. 20 shows the maximum fractional Hamiltonian component as a function of probe 10 height for three different spin samples. The measurement window is defined between the decoherence rate and the measurement bandwidth. The probe height can vary over almost 100 nm and still provide a detectable signal. The FIG. 20 insert is a diagram that illustrates the simplified magnetic dipolar coupling model, which depends on the separation, orientation and magnetic moment of 5 both the probe and sample spins.

Figure 21:
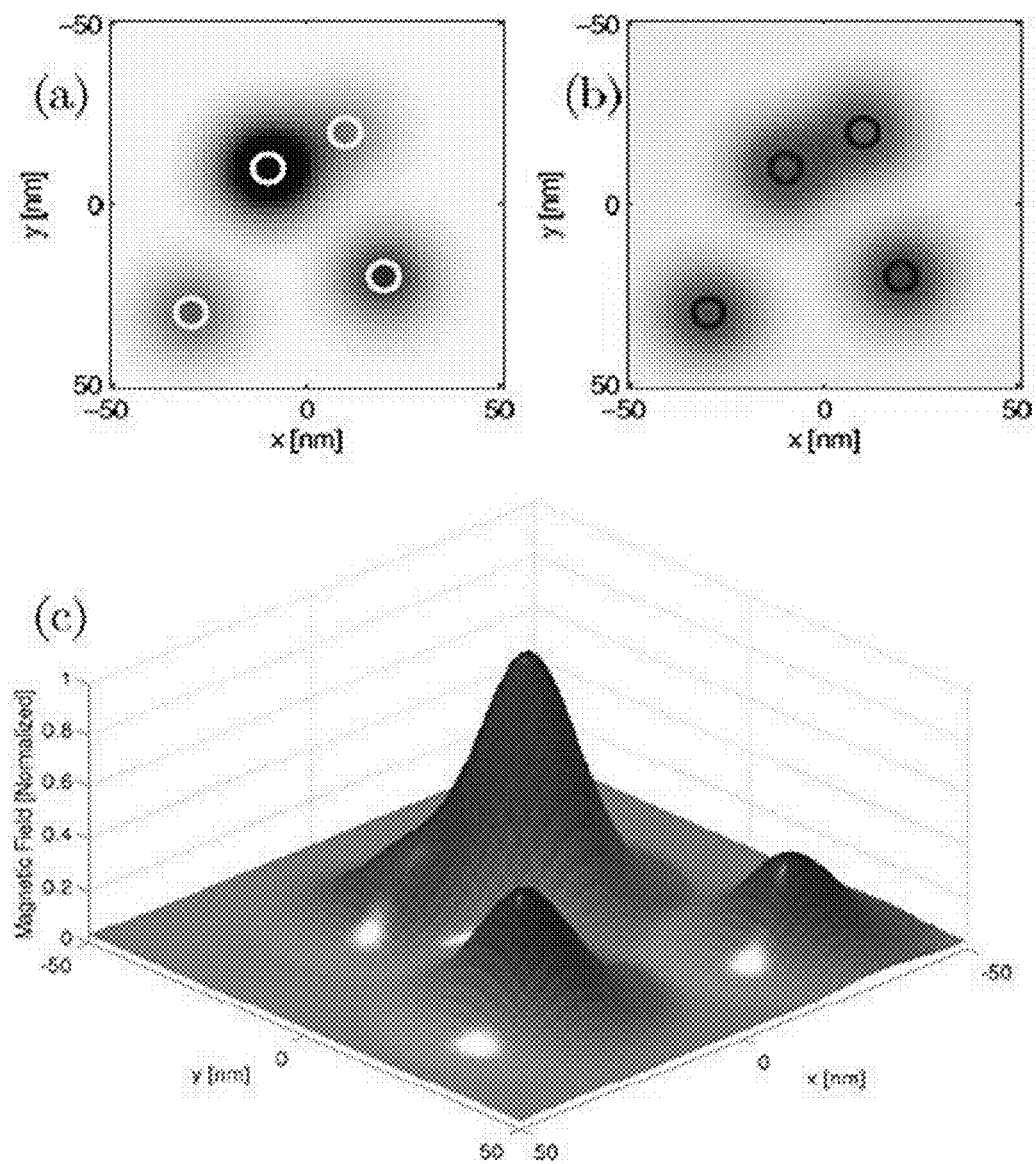
FIG. 21(a) is a plot of magnetic field strength as measured via the variation in the probe qubit Hamiltonian. The pixel intensity represents the normalized fractional variation in the probe spin Hamiltonian.
FIG. 21(b) is a plot of the effective temperature of each spin, based on the population of the ground and excited states.
FIG. 21(c) is a surface plot of the magnetisation with shading based on the fraction of time spent in the excited spin state of the sample spin.

In FIG. 21, we create an image from a fictitious sample consisting of 4 mesoscopic spins with varying net magnetisation. We assume the spins are in thermal equilibrium with the sample substrate (which we have set at T=4K) and that they are flipping due to thermal processes[52]. The white/black circles indicate the position and diameter (8 nm) of the sample spin and enclosing molecules. The detection limits discussed earlier for maximum and minimum detectable field are included in this calculation.

The magnetisations are $M_0$=50, 70, 100 and 200$\mu_B$ and the average population of the excited state is given by a Boltzmann distribution for a background magnetic field of B=0.1 T and temperature T=4K. The spatial resolution of the probe position is a 50×50 grid, giving 2500 points over 10000 $nm^2$ and the probe height was set to $h_p$=20 nm.

FIG. 21(a) shows the measured magnetic field over the sample. Note that the probe in this mode (purely acting as a magnetometer) does not successfully resolve two of the spins.

FIG. 21(b) shows the measured decoherence field over the same sample. As each spin has a different magnetisation, the decoherence effects (in this case splitting of the Rabi peak) resulting from each spin are different. The ratio of the two split peaks provides the population of the spin states, which is in turn directly related to the magnetisation and effective temperature of the sample spin.

In this plot, the ratio of the split peaks has been used to code the data, with deep shading indicating both a large spin magnetisation (or low effective temperature) and a small magnetisation (high temperature). The intensity of the shading is given purely by the amount of signal available from each decoherence source (compared to the probe spin's intrinsic decoherence), whereas in FIG. 4(a), the intensity was proportional to the total induced field. Colour coding could again be used to differentiate the large and small magnetisations.

Finally, we can combine this data to produce a plot showing the field intensity with each decoherence source (mesoscopic spin) tagged based on its effective temperature. This is shown in FIG. 21(c) where the existence of all four spins can be detected based on the height (two are merged), in contrast to the magnetometer scan alone where only two spins were detected. The height and greyscale are normalised as per (a) and (b) respectively. The flat area corresponds to a region where the Rabi splitting is not large enough to resolve the spin populations with these measurement parameters.

While we have demonstrated that new information can be obtained by looking at the induced decoherence, this is only useful if the information can be obtained within an experimentally accessible time. Using the measurement model discussed earlier, we can estimate the parameter uncertainties in the Hamiltonian characterisation process. Retaining the parameters from Example II, we calculate the noise expected for a finite dwell time ($t_{dwell}$) on each pixel and the total image acquisition time ($t_a$).

Figure 22:
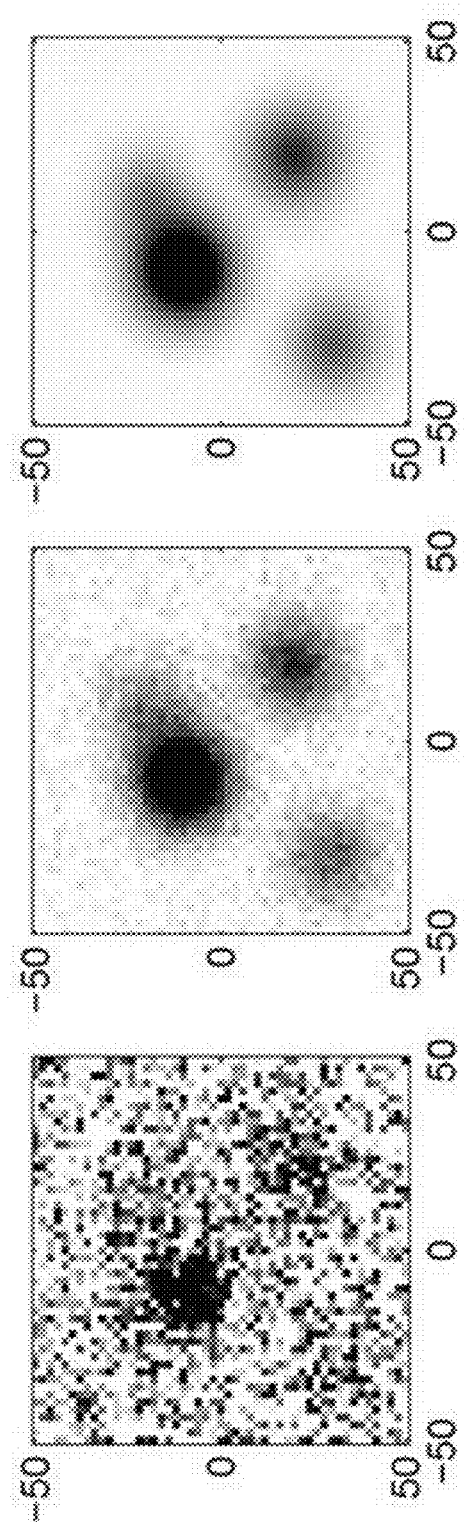
FIG. 22 is a series of pixilated plots relating to the image of FIG. 21(a) with simulated noise stemming from a finite measurement time; The images from left to right simulate dwell times of $t_{dwell}$=2 µs, 200 µs and 20 ms.

FIG. 22 relates to FIG. 21(a) with the noise resulting from a finite bandwidth and dwell time. The images from left to right simulate dwell times of $t_{dwell}$=2 μs, 200 μs and 20 ms, which give a total acquisition time for a 50×50 grid (2500 pixels) of $t_a$=5 ms, 0.5 s and 15 50 s respectively. The average pixel error variance is $10^{-1}$, $10^{-3}$ and $10^{-5}$ for the three images respectively.

It should be noted that this ignores the effect of noise induced in the detection setup. This additional noise will contribute directly to the measured response spectrum and will add directly to the measurement variance. The result is an increase in measurement times but, provided the detector noise is characterised, this does not restrict the systems ability to characterise the probe and therefore the sample.

To allow fast image acquisition times, it is important to have both large detector bandwidth and a large ratio of bandwidth to intrinsic decoherence rate $BW/\Gamma q$. The qubit transition frequency is less important, provided it is at least an order of magnitude greater than the intrinsic decoherence. However, a tunable qubit frequency is advantageous as many types of decoherence depend strongly on the frequency at which they are probed.

Embodiments of the present invention provide a fundamentally new and complementary imaging mode which takes advantage of current qubit technology and modern techniques for characterising few-state quantum systems. Mapping the induced decoherence across a sample effectively images the dynamics of the environment, providing a new window into the microscopic world with wide applications to spin and charge fluctuations and transport in both solid-state and biological systems.

Method: Example I

Decoherence Due to a Bath of 1/F Fluctuators

We wish to use a simple model of the decoherence felt by a probe (charge–)qubit interacting with a bath of 1/f fluctuators[23,24,33]. The numerical parameters used for such a model vary greatly depending on the system and even from sample to sample. Here we are interesting in the functional dependence, rather than the explicit values. We draw heavily from references [33] and [24] as an example.

Consider a qubit interacting with a bath of fluctuators via an interaction Hamiltonian $H_{int}$ which has the form $$H_{int} = \sigma_z \sum_j v_j b_j^\dagger b_j \quad (14)$$

where $\sigma_z$ acts on the qubit and $b_j$ destroys (creates) an electron in a localized state in the bath.

The spectral response from the $j^{th}$ fluctuator (in the fast fluctuator limit) is given by $$s_j(\omega) \propto \frac{v_j^2 \gamma_j}{\gamma_j^2 + \omega^2} \quad (15)$$

where $v_j$ is the strength of the fluctuator which fluctuates with rate $\gamma_j$. The total spectral response is then the sum over each of the fluctuators $$S(\omega) = \Sigma_j s_j(\omega) \quad (16)$$

and a simplified Golden rule model gives the relaxation rate $(\Gamma_2^{GR})$ and dephasing rate as $$\Gamma_2^{GR} = \frac{1}{2} \Gamma_-^{GR} = \frac{1}{4} S(E_j) \quad (17)$$

where $E_J$ is the tunnelling energy of the qubit. Given a functional form for how $v_j(r)$ 30 depends on the fluctuator/qubit separation r, we can then compute the effective decoherence rate felt by the qubit.

Method: Example II

Magnetic Dipolar Coupling Between a Probe and Sample Spin

For this analysis, we will use a simplified (but quite general model) consisting of a probe spin interacting via the magnetic dipolar interaction with a much larger sample spin (see insert of FIG. 20). The sample spin can be considered as a Ferritin, $Fe_8$ or other mesoscopic molecule with a net magnetic moment $M_0 \gg 1\mu_B$. As the spin is large (and to simplify the analysis of decoherence) we will assume that it is in thermal equilibrium with the sample environment and therefore the average magnetisation and spin flip rates are given by the standard thermodynamic quantities. In making this assumption, we ignore quantum mechanical effects between the probe and sample spins and treat the effect of the sample spin on the probe as a fluctuating classical field.

The magnetic dipolar interaction is given by[14]

$$H_{dip} = \left(\frac{\mu_0}{4\pi}\right) \hbar^2 \gamma_p \gamma_s \left[\frac{\vec{P} \cdot \vec{S}}{r^3} - \frac{3(\vec{P} \cdot \vec{r})(\vec{S} \cdot \vec{r})}{r^5}\right] \quad (18)$$

where $\gamma_p$ and $\gamma_s$ are the probe and sample spin gyromagnetic ratios, rr is the vector separation between the spins and P and S are the probe and sample spin operators.

We assume the system is bathed in a global magnetic field $B_{global}$ which orientates both the sample and probe spins[53] and sets their energy scales. The dipolar interaction is then given by the separation between the spins r and the angle subtended between the spin orientation and the vector separating the spins $\phi$, as illustrated in the insert to FIG. 14. The simplified coupling Hamiltonian is then given by $$H_{dip} = \left(\frac{\mu_0}{4\pi}\right)\left(\frac{\hbar^2 \gamma_p \gamma_s}{r^3}\right)(3\cos^2\phi - 1)P_z \cdot S_z \quad (19)$$

which is a purely Ising type interaction whose strength depends on both the separation and angle between the spins. The perturbing effect of this dipolar Hamiltonian can then be measured in the spectral response of the qubit, giving an direct link to both the spin state and magnetisation of the sample spin.

REFERENCES

All the following references are incorporated herein by reference.

1. B. M. Chernobrod and G. P. Berman, J. Appl. Phys. 97, 014903 (pages 3) (2005).
2. E. Il'ichev and Y. S. Greenberg, Euro. Phys. Lett. 77, 58005 (5 pp) (2007).
3. V. I. Shnyrkov and S. I. Melnik, Low Temp. Phys. 33, 15 (2007).
4. R. DeSousa, arXiv:cond-mat/0610716 (2006).
5. M. A. Nielsen and I. L. Chuang, Quantum computation and quantum information (Cambridge University Press, Cambridge, 2000).

6. M. Paris and J. Rehacek, Quantum state estimation, Lecture notes in physics, 649. (Springer, Berlin; New York, 2004).
7. M. Mohseni, A. T. Rezakhani, and A. Aspuru-Guzik, Phys. Rev. A 77, 042320 (pages 5) (2008).
8. S. G. Schirmer, A. Kolli, and D. K. L. Oi, Phys. Rev. A 69, 050306(R) (2004).
9. J. H. Cole, S. G. Schirmer, A. D. Greentree, C. Wellard, D. K. L. Oi, and L. C. L. Hollenberg, Phys. Rev. A 71, 062312 (2005).
10. J. H. Cole, A. D. Greentree, D. K. L. Oi, S. G. Schirmer, C. J. Wellard, and L. C. L. Hollenberg, Phys. Rev. A 73, 062333 (2006).
11 J. H. Cole, S. J. Devitt, and L. C. L. Hollenberg, J. Phys. A 39, 14649 (2006).
12 S. J. Devitt, J. H. Cole, and L. C. L. Hollenberg, Phys. Rev. A 73, 052317 (2006).
13 T. F. Jordan, A. Shaji, and E. C. G. Sudarshan, Phys. Rev. A 76, 012101 (pages 6) (2007).
14 C. P. Poole and H. A. Farach, The theory of magnetic resonance (WileyInterscience, New York, 1972).
15 T. A. Brun, Am. J. Phys. 70, 719 (2002).
16 C. W. Gardiner, Quantum noise, Springer series in synergetics; v. 56. (Springer-Verlag, Berlin; New York, 1991).
17 M. O. Scully and M. S. Zubairy, Quantum optics (Cambridge University Press, Cambridge, 2006).
18 A. N. Korotkov and D. V. Averin, Phys. Rev. B 64, 165310 (2001).
15 19 Q. Zhang, R. Ruskov, and A. N. Korotkov, Phys. Rev. B 72, 245322 (pages 11) (2005).
20 N. P. Oxtoby, H. M. Wiseman, and H.-B. Sun, Phys. Rev. B 74, 045328 (pages 11) (2006).
21 N. P. Oxtoby, J. Gambetta, and H. M. Wiseman, Phys. Rev. B 77, 125304 (pages 11) (2008).
22 K. S. Birdi, Scanning Probe Microscopes: Applications in Science and Technology (CRC Press, Boca Raton; London; New York; Washington D.C., 2003).
23 J. Schriefl, Y. Makhlin, A. Shnirman, and G. Schon, New J. Phys. 8, 1 (2006).
24 Y. M. Galperin, B. L. Altshuler, J. Bergli, and D. V. Shantsev, Phys. Rev. Lett. 96, 25 097009 (pages 4) (2006).
25 D. Loss and D. P. DiVincenzo, Phys. Rev. A 57, 120 (1998).
26 L. C. L. Hollenberg, A. S. Dzurak, C. Wellard, A. R. Hamilton, D. J. Reilly, G. J. Milburn, and R. G. Clark, Phys. Rev. B 69, 113301 (2004).
27 Y. Makhlin, G. Schon, and A. Shnirman, Rev. Mod. Phys. 73 357 (2001).
28 J. Q. You, X. Hu, S. Ashhab, and F. Nori, Phys. Rev. B 75, 140515 (pages 4) (2007).
29 J. Koch, T. M. Y., J. Gambetta, A. A. Houck, D. I. Schuster, J. Majer, A. Blais, M. H. Devoret, S. M. Girvin, and R. J. Schoelkopf, Phys. Rev. A 76, 042319 (pages 19) (2007).
30 Y. Nakamura, Y. A. Pashkin, and J. S. Tsai, Nature 398, 786 (1999).
31 T. Yamamoto, Y. A. Pashkin, O. Stafiev, Y. Nakamura, and J. S. Tsai, Nature 425, 941 (2003).
32 J. Majer, J. M. Chow, J. M. Gambetta, J. Koch, B. R. Johnson, J. A. Schreier, L. Frunzio, D. I. Schuster, A. A. Houck, A. Wallraff, et al., Nature 449, 443 (2007).
33 E. Paladino, L. Faoro, G. Falci, and R. Fazio, Phys. Rev. Lett. 88, 228304 (2002).
34 D. D. Awschalom, J. F. Smyth, G. Grinstein, D. P. DiVincenzo, and D. Loss, Phys. Rev. Lett. 68, 3092 (1992).
35 J. Tejada, X. X. Zhang, E. del Barco, J. M. Hernandez, and E. M. Chudnovsky, Phys. Rev. Lett. 79, 1754 (1997).
36 E. d. Barco, J. M. Hernandez, J. Tejada, N. Biskup, R. Achey, I. Rutel, N. Dalal, and J. Brooks, Phys. Rev. B 62, 3018 (2000).
37 D. Rugar, R. Budakian, H. J. Mamin, and C. B. W., Nature 430, 329 (2004).
38 H. G. Hansma and J. H. Hoh, Ann. Rev. Biophys. Biomol. Struct. 23, 115 (1994).
39 C. I. Pakes, D. P. George, S. Ramelow, A. Cimmino, D. N. Jamieson, and S. Prawer, J. Mag. Mag. Mat. 272-276 (1), E1231 (2004).
40 F. Jelezko, C. Tietz, A. Gruber, I. Popa, A. Nizovtsev, S. Kilin, and J. Wrachtrup, Single Mol. 2, 255 (2001).
41 F. Jelezko, T. Gaebel, I. Popa, A. Gruber, and J. Wrachtrup, Phys. Rev. Lett. 92, 076401 (2004).
42 F. Jelezko, T. Gaebel, I. Popa, M. Domhan, A. Gruber, and J. Wrachtrup, Phys. Rev. Lett. 93, 130501 (2004).
43 F. T. Charnock and T. A. Kennedy, Phys. Rev. B. 64, 041201 (2001).
44 T. A. Kennedy, F. T. Charnock, J. S. Colton, J. E. Butler, R. C. Linares, and P. J. Doering, Phys. Status Solidi B 233, 416 (2002).
45 T. Gabel, M. Domhan, I. Popa, C. Wittmann, P. Neumann, F. Jelezko, J. R. Rabeau, N. Stavrias, A. D. Greentree, S. Prawer, et al., Nat. Phys. 2, 408 (2006).
46 R. Hanson, F. M. Mendoza, R. J. Epstein, and D. D. Awschalom, Phys. Rev. Lett. 97, 087601 (2006).
47 P R. Hanson, V. V. Dobrovitski, A. E. Feiguin, O. Gywat, and D. D. Awschalom, Science 320, 352 (2008).
48 J. Wrachtrup and F. Jelezko, J. Phys. Cond. Matt. 18, S807 (2006). 20
49 A. N. Korotkov, Phys. Rev. B 63, 085312 (2001).
50 In general, any given qubit measurement system requires a more detailed and specific model. Here we present an architecture independent discussion and therefore avoid more complicated treatments.
51 This means operating well above the Korotkov-Averin bound 18,49 so that the 25 sample decoherence effects dominate the signal The exact details of the flipping process are unimportant for this example. We assume they are dominated by thermal processes and obey Boltzmann statistics
53 We ignore the effects of crystal field terms on both the orientation of the sample and probe spin, though this does not decrease the generality of the result 30
54 C. L. Degen, Appl. Phys. Lett. 92, 243111 (2008). [theory proposal]
55 J. M. Taylor, P. Cappellaro, L. Childress, L. Jiang, D. Budker, P. R. Hemmer, A. Yacoby, R. Walsworth, and M. D. Lukin, Nature Physics, Advance online publication doi: 10.1038/nphys1075 (2008). [theory proposal]
56 J. R. Maze, P. L. Stanwix, J. S. Hodges, S. Hong, J. M. Taylor, P. Cappellaro, L. Jiang, M. V. Gurudev Dutt, E. Togan, A. S. Zibrov, A. Yacoby, R. L. Walsworth, M. D. Lukin Nature 455, 644-647 (2 Oct. 2008), doi: 10.1038/nature07279, [experimental demo]
57 G. Balasubramanian, I. Y. Chan, R. Kolesov, M. Al-Hmoud, J. Tisler, C. Shin, C. 40 Kim, A. Wojcik, P. R. Hemmer, A. Kruger, T. Hanke, A. Leitenstorfer, R. Bratschitsch, F. Jelezko, and J. Wrachtrup, Nature 455, 648-651 (2 Oct. 2008), doi: 10.1038/nature07278. [experimental demonstration]
65 K. Lundstrom. *Cell. Mol. Life Sci.*, 63:2597-2607, 2006.
66 B. Hillle. *Ionic Channels of Excitable Membranes*. Sinauer Associates, Sunderland, Mass., 3 edition, 2005.
67 Y. Fang and A. Frutos and J. Lahiri. *J. Am. Chem. Soc*, 124(1):2394-2395, 2002.
68 V. Yamazaki and others. *BMC Biotechnol.*, 5:18, 2005.

69 E. Reimhult and K. Kumar. *Trends Biotechnol.*, 26:82-89, 2008.
70 R. Jelinek and L. Silbert. *Mol. Biosyst.*, 5:811-818, 2009.
71 A. Demuro and I. Parker. *J. Gen. Physiol.*, 126:179-192, 2005.
72 G. Balasubramanian and others. *Nature*, 455:648-651, 2008.
73 F. Neugart and others. *Nano Lett.*, 7:3588-3591, 2007.
74 C. C. Fu and others. *Proc. Natl. Acad. Sci. U.S.A.*, 104(3): 727-732, 2007.
75 J. Chao and others. *Biophys. J.*, 94:2199-2208, 2007.
76 O. Faklaris and others. *Small*, 4(12):2236-2239, 2008.
77 A. S. Barnard. *Analyst*, 134(9):1729-1940, 2009.
78 J. H. Cole and L. C. L. Hollenberg. arXiv:0811.1913v1 [quant-ph], 73:062333, 2008.
79 B. M. Chernobrod and G. P. Berman. *J. Appl. Phys.*, 97:014903, 2004.
80 C. L. Degen. *Appl. Phys. Lett.*, 92:243111, 2008.
81 J. M. Taylor and others. *Nature Phys.*, 4:810-816, 2008.
82 J. R. Maze and others. *Nature*, 455:644-647, 2008.
83 G. Balasubramanian and others. *Nature Mat.*, 8:383-387, 2009.
84 L. T. Hall and others. arXiv:0907.2292v1 [cond-mat.meshall], 73:062333, 2009.
85 T. Ide and others. *Jpn. J. Physiol.*, 52:429, 2002.
86 G. Baaken and others. *Lab Chip*, 8:938-944, 2008.
87 S. Damjanovich. *Biophysical Aspects of Transmembrane Signalling*. Springer-Verlag, Berlin, Heidelberg, 1 edition, 2005.
88 E. Fenwick and A. Marty and E. Neher. *J. Physiol*, 331: 599-635, 1982.
89 M. Quick. *Transmembrane Transporters*. Johnn Wiley & Sons, Inc, Hoboken, N.J., 1 edition, 2002.
90 P. Mueller and others. *Nature*, 194:979-980, 1962.
91 P. Mueller and others. *J. Phys. Chem.*, 67:534-535, 1962.
92 S. J. Yu and others. *J. Am. Chem. Soc*, 127(50):17604-17605, 2005.
93 A. M. Schrand and others. *J. Phys. Chem. B. Lett.*, 111:2-7, 2006.
94 F. Jelezko and others. *Appl. Phys. Lett.*, 81:2160-2162, 2002.
95 F. Jelezko and J. Wrachtrup. *Phys. Stat. Sol.*, 203:3207-3225, 2006.
96 F. Jelezko and others. *Phys. Rev. Lett.*, 92:3207-3225, 2004.
97 R. Hanson and others. *Science*, 320:352-355, 2008.
98 H. Leontiadou and others. *Biophys. J.*, 92:4209-4215, 2007.
99 Vladimir I. Tikhonov and Alexander A. Volkov. *Science*, 296:2363, 2002.
100 H. Bannai and others. *Nature Protocols*, 1:2628-2634, 2006.
101 E. van Oort and M. Glasbeek. *Chem. Phys. Lett.*, 168(6): 529-532, 1990.
102 Y. C. Kim and M. E. Fisher. *Phys. Rev. E*, 77:051502, 2008.
103 J. A. Formes. *J. Colloid Interface Sci.*, 222:97-102, 2000.
104 V. M. Acosta and others. *Phys. Rev. B*, 80(11):115202, 2009.
105 P. Arhem and C. Blomberg. *Biosystems*, 89:117-125, 2007.

The references are incorporated herein by reference.

Reference that is being made to references 1 to 105 does not constitute and admission that these references are part of the common general knowledge in any country.

Although the invention has been described with reference to a particular example, it should be appreciated that it could be exemplified in many other forms and in combination with other features not mentioned above.

The invention claimed is:

1. A method of monitoring a property of a sample, the method comprising the steps of:
   providing a quantum probe having a quantum state;
   exposing the quantum probe to the sample in a manner such that the property of the sample, in the proximity of the quantum probe, affects quantum coherence of the quantum probe; and
   detecting a rate of quantum decoherence of the quantum probe to monitor the property of the sample.

2. The method of claim 1 wherein the property is a nanoscopic property.

3. The method of claim 2 wherein the nanoscopic property relates to a fundamental spin or charge, or collections thereof.

4. The method of claim 1 wherein the quantum probe comprises a two-state (qubit) or multi-state quantum probe.

5. The method of claim 1 wherein the quantum probe comprises a diamond material having at least one nitrogen-vacancy (NV) centre.

6. The method of claim 1 wherein the step of providing the quantum probe comprises transforming the quantum probe into a predefined quantum state.

7. The method of claim 1 comprising the step of controlling the quantum state of the quantum probe by applying suitable radiation.

8. The method of claim 1 wherein the step of providing the quantum probe comprises transforming the quantum probe into a superposition or entangled state.

9. The method of claim 8 wherein transforming the quantum probe comprises the application of suitable radiation.

10. The method of claim 9 wherein the quantum probe comprises a NV centre and wherein the step of transforming the quantum probe comprises exposing the NV-centre to suitable microwave radiation to generate a suitable quantum state of the Zeeman energy levels.

11. The method of claim 10 comprising optically pumping the NV-centre.

12. The method of claim 10 wherein the step of detection a decoherence rate comprises detecting fluorescence photons emitted from the NV-centre.

13. The method of claim 1 comprising the step of moving the quantum probe and the sample relative to each other and performing the method so that the decoherence rate is detectable at a plurality of sample locations.

14. The method of claim 1 comprising detecting fluctuations or particles in the surface or bulk of a biological sample.

15. The method of claim 14 wherein the biological sample includes ion channels and wherein the method comprises detecting an increase in quantum decoherence rate caused by an influence of a spin of ion on the quantum probe and thereby monitoring the function of the ion channel.

16. The method of claim 1 wherein the step of detecting a rate of quantum decoherence comprises detecting photons emitted from the plurality of quantum probes.

17. An apparatus for monitoring a property of a sample, the apparatus comprising:
    a quantum probe that has quantum state;
    a holder for holding the quantum probe in the proximity of a sample so that the quantum coherence of the quantum probe is influenced by the property of the sample; and
    a detector for detecting a quantity indicative of a quantum decoherence rate and thereby monitoring the property of the sample.

18. The apparatus of claim 17 wherein the property of the sample is a nanoscopic property of the sample.

19. The apparatus of claim 17 wherein the quantum probe comprises one quantum system.

20. The apparatus of claim 17 wherein the quantum probe comprises a plurality of quantum systems.

21. The apparatus of claim 17 wherein the quantum probe is movable relative to the sample.

22. The apparatus of claim 17 wherein the quantum probe is incorporated in the sample.

23. The apparatus of claim 17 wherein the holder comprises a scanning arrangement that is suitable for scanning the quantum probe and the sample relative to each other.

24. The apparatus of claim 17 wherein the quantum probe comprises a diamond material having one or a plurality of nitrogen-vacancy (NV) centres.

25. The apparatus of claim 24 comprising an optical light source for optically pumping the at least one NV-centre.

26. The apparatus of claim 17 comprising a source for transforming the quantum probe into the quantum state.

27. The apparatus of claim 17 comprising a source for controlling the quantum state of the quantum probe.

* * * * *